US012171833B2

(12) United States Patent
Schmitt et al.

(10) Patent No.: US 12,171,833 B2
(45) Date of Patent: Dec. 24, 2024

(54) MUCOADHESIVE POLYMERIC DRUG DELIVERY COMPOSITIONS AND METHODS

(71) Applicant: The University of British Columbia, Vancouver (CA)

(72) Inventors: Veronika Schmitt, Vancouver (CA); John K. Jackson, West Vancouver (CA); Martin E. Gleave, Vancouver (CA); Claudia Kesch, Essen (DE)

(73) Assignee: The University of British Columbia, Vancouver (CA)

( * ) Notice: Subject to any disclaimer, the term of this patent is extended or adjusted under 35 U.S.C. 154(b) by 190 days.

(21) Appl. No.: 17/797,627

(22) PCT Filed: Feb. 6, 2021

(86) PCT No.: PCT/CA2021/050136
§ 371 (c)(1),
(2) Date: Aug. 4, 2022

(87) PCT Pub. No.: WO2021/155477
PCT Pub. Date: Aug. 12, 2021

(65) Prior Publication Data
US 2023/0042600 A1    Feb. 9, 2023

Related U.S. Application Data

(60) Provisional application No. 62/971,882, filed on Feb. 7, 2020.

(51) Int. Cl.
*A61K 47/34* (2017.01)
*A61K 9/00* (2006.01)
(Continued)

(52) U.S. Cl.
CPC ............ *A61K 47/34* (2013.01); *A61K 9/0034* (2013.01); *A61K 31/337* (2013.01);
(Continued)

(58) Field of Classification Search
CPC .. A61K 47/34; A61K 9/0034; A61K 31/7068; A61K 47/10; A61K 47/32; A61K 47/36; C08L 7/02; C08L 5/08
See application file for complete search history.

(56) References Cited

U.S. PATENT DOCUMENTS

| | | | |
|---|---|---|---|
| 10,471,150 B2 | 11/2019 | Konorty et al. | |
| 2004/0151774 A1 | 8/2004 | Pauletti et al. | |
| 2008/0299220 A1* | 12/2008 | Tamarkin ............ | A61K 31/047 514/474 |

FOREIGN PATENT DOCUMENTS

| | | |
|---|---|---|
| WO | WO 2016/019627 | 2/2016 |
| WO | WO 2018/227293 | 12/2018 |
| WO | WO 2020/014623 | 1/2020 |

OTHER PUBLICATIONS

Kesch et al., (2021) "A Polymeric Paste-Drug Formulation for Local Treatment of Upper Tract Urothelial Carcinoma", Urologic Oncology: Seminars and Original Investigations, vol. 39(3), pp. 194. e1-194. e7.

(Continued)

*Primary Examiner* — Carlos A Azpuru
(74) *Attorney, Agent, or Firm* — Rudy J. Ng; Bozicevic, Field & Francis LLP

(57) ABSTRACT

This invention provides compositions for controlled localized depositing of one or more drugs within a subject. More particularly, described herein are compositions comprising a) a polyethylene glycol (PEG) composition having a first low molecular weight PEG (Mw between 200-500 Da) and a second low molecular weight PEG (Mw between 500-2000 Da) and b) a mucoadhesive in polymer. Alternatively, composition may comprise a) a polyethylene glycol (PEG) composition having a first low molecular weight PEG (Mw between 200-500 Da) and a second low molecular weight PEG (Mw between 500-2000 Da), b) a water insoluble (Continued)

polymer and c) a mucoadhesive polymer. Furthermore, the composition may further comprise one or more drugs. Also provided are methods of manufacturing and administering the compositions described herein, which are used as biodegradable, injectable mucoadhesive low-viscosity pastes.

20 Claims, 6 Drawing Sheets

(51) Int. Cl.
    *A61K 31/337*     (2006.01)
    *A61K 31/7068*    (2006.01)
    *A61K 47/10*     (2017.01)
    *A61K 47/32*     (2006.01)
    *A61K 47/36*     (2006.01)

(52) U.S. Cl.
    CPC .......... *A61K 31/7068* (2013.01); *A61K 47/10* (2013.01); *A61K 47/32* (2013.01); *A61K 47/36* (2013.01)

(56) References Cited

OTHER PUBLICATIONS

Athanasiou et al., (1996) "Sterilization, toxicity, biocompatibility and clinical applications of polylactic acid/polyglycolic acid copolymers," Biomaterials, 17(2): 93-102.

Bouissou et al., (2006) "The Influence of Surfactant on PLGA Microsphere Glass Transition and Water Sorption: Remodeling the Surface Morphology to Attenuate the Burst Release," Pharmaceutical Research, 23(6): 1295-1305.

Dunn (2003) "The Atrigel Drug Delivery System," Marcel Dekker Inc., 647-655.

Jackson et al., (2000) "The Suppression of Human Prostate Tumor Growth in Mice by the Intratumoral Injection of a Slow-Release Polymeric Paste Formulation of Paclitaxel," Cancer Research, 60: 4146-4151.

Jackson et al., (2004) "Characterization of perivascular poly(lactic-co-glycolic acid) films containing paclitaxel," International Journal of Pharmaceutics, 283: 97-109.

Jackson et al., (2004) "The characterization of novel polymeric paste formulations for intratumoral delivery," International Journal of Pharmaceutics, 270: 185-198.

Jackson et al., (2007) "The characterization of paclitaxel-loaded microspheres manufactured from blends of poly (lactic-co-glycolic acid) (PLGA) and low molecular weight deblock copolymers," International Journal of Pharmaceutics, 342: 6-17.

Jain et al., (2000) "The manufacturing techniques of various drug loaded biodegradable poly(lactide-co-glycolide) (PLGA) devices," Biomaterials, 21: 2475-2490.

Makadia and Siegel (2011) "Poly Lactic-co-Glycolic Acid (PLGA) as Biodegradable Controlled Drug Delivery Carrier," Polymers, 3: 1377-1397.

Roy et al., (2009) "Polymers in Mucoadhesive Drug-Delivery Systems: A Brief Note," Designed Monomers and Polymers, 12: 483-495.

Schmitt et al., (2019) "Local Delivery of Chemotherapy: Development of a New Drug Formulation for the Instillation into the Renal Pelvis," NWUS, 1 page.

Siegel et al., (2006) "Effect of drug type on the degradation rate of PLGA matrices," European Journal of Pharmaceutics and Biopharmaceutics, 64: 287-293.

Winternitz et al., (1996) "Development of a Polymeric Surgical Paste Formulation for Taxol," Pharmaceutical Research, 13(3): 368-375.

Zhang et al., (1996) "Development of amphiphilic diblock copolymers as micellar carriers of taxol," International Journal of Pharmaceutics, 132: 195-206.

\* cited by examiner

MUCOADHESIVE POLYMERIC DRUG DELIVERY COMPOSITIONS AND METHODS

CROSS REFERENCE TO RELATED APPLICATION

This application claims the benefit of U.S. Provisional Patent Application Ser. No. 62/971,882 filed on 7 Feb. 2020, entitled "MUCOADHERSIVE POLYMERIC DRUG DELIVERY COMPOSITIONS AND METHODS".

FIELD OF THE INVENTION

This invention relates to biodegradable polymeric low-viscosity pastes suitable for drug delivery. More particularly, the invention relates to injectable mucoadhesive polymeric low-viscosity pastes comprising a polyethylene glycol (PEG) composition, a water insoluble polymer and a mucoadhesive polymer. Furthermore, the composition may further comprise one or more drugs that release in a controlled manner.

BACKGROUND OF THE INVENTION

Local Drug Treatment by Injection into the Renal Pelvis
Renal disease and renal abnormalities are generally difficult to treat. Most renal drug treatments require the administration of high drug concentrations systemically, that may be associated with adverse effects, like abnormal glomerular filtration, tubular secretion or proteinuria. Furthermore, high systemic drug concentrations may not translate into high concentrations in the target cell and the distribution of drugs to the kidney may be insufficient to meet therapeutic goals. Accordingly, kidney-targeted drug delivery is often needed in treating renal disease. Untreated or improperly treated renal disease often requires dialysis, long-term medication or even kidney transplantation to prolong life.

Intravesical administration of anti-cancer drugs has reduced recurrence and progression of bladder cancer. However, the delivery of drugs to treat malignancies of the renal pelvis and ureter is challenging. The constant flow of urine through the upper and lower urinary tract washes away locally administered drug and the only curative treatment for urothelial carcinoma of the renal pelvis or ureter is surgery.

Upper Tract Urothelial Carcinoma

Urothelial carcinomas (UCs) may occur in the lower urinary zones (bladder or urethra) or in the upper urinary tract (UUT: pyelocaliceal cavities and ureter) (Lughezzani et al. 2012). Over 90% of UCs are located in the bladder with under 10% occurring in the upper tract (UTC). Patients with bladder cancer are usually diagnosed with early stage disease and the cancer confined to the superficial urothelium. This is partly due to the easy access of diagnostic equipment via the urethra. However, many patients with UTCs are not diagnosed early and may have already progressed to invasive disease. Staging of UTCs may also be difficult as the tissue is fragile with only limited musculature so that biopsies do not always accurately describe the disease level.

Once diagnosed, radical nephroureterectomy (RNU) with bladder-cuff removal is considered the standard treatment of UTC (Audenet et al. 2013; Roupret et al. 2013). This procedure involves full removal of the kidney, the ureter and the bladder cuff. Tumor cell spillage may be a problem with such procedures. Furthermore, many patients are not candidates for this treatment. Some patients with low-risk disease, may be offered a more conservative treatment such as endoscopic ablation or segmental removal (Lughezzani et al. 2012). Clearly, with later diagnosis, the prognosis for these patients with UTC is poor. Chemotherapeutic options are limited for these patients especially because cisplatin based regimens are associated with nephrotoxicity, which may be exacerbated, when one kidney is removed. Other drugs used to treat bladder cancer such as Mitomycin C and Gemcitabine may have a preferred toxicity profile. When used to treat bladder cancer these drugs may be delivered at high concentrations intravesically (directly into the bladder) so that a 2 hour retention allows reasonable drug uptake into the tissues after tumor resection. More recently, the drug docetaxel is under investigation as a chemotherapeutic option to treat bladder cancer locally and UTC by systemic delivery. The combination of gemcitabine and docetaxel, is also being studied as an improvement to using either drug alone (Gitlitz et al. 2003).

Because the UUT tissues cannot be treated locally with a drug solution (the pelvis is accessible but drug solutions would quickly wash into the bladder) one company, UroGen Pharma, Inc.™, has developed a gel formulation of mitomycin called JELMYTO™ (Mitogel™). This gel undergoes a thermo-reversible gel transition in the body so may be injected as a liquid to form a semi solid gel in the pelvis of the kidney. The pluronic-based gel dissolves slowly, but allows for some retention of the drug in the tissues at the target site.

Injectable Polymeric Paste

Drugs are normally delivered orally or by injection to allow systemic uptake and circulation to most parts of the body. For many drugs this route of administration is ideally suited, for example, insulin for diabetes or statins for heart disease. However, many diseases are localized and the preferred method is to deliver the drug directly to the site of action. For example, painkillers for chronic localized pain, anticancer drugs for local tumors and anti-arthritic drugs to relieve symptoms of arthritis and joint pain. Accordingly, there have been numerous attempts to design locally injectable systems to deliver drugs to specific body sites. This targeted approach may also minimize systemic toxicity often associated with conventional methods of delivering drugs. The intravenous delivery of anticancer drugs often causes severe side effects and systemic toxicities usually limit drug dose. Local polymeric drug delivery systems could mitigate systemic side effects and allow for the delivery of high local doses.

Poly(DL-lactide-co-glycolide) (PLGA) is a common constituent of polymeric drug delivery systems. It is an FDA-approved biopolymer of lactic acid (D,L-LA) and glycolic acid (GA) and has been used both as a drug delivery carrier and as a scaffold for tissue engineering (Bouissou et al. 2006; Jain 2000). The degradation of PLGA depends on many factors including, but not limited to, the ratio of LA to GA, crystallinity, weight average molecular weight of the polymer, shape of the matrix, and type and amount of drug incorporated (Siegel et al. 2006; Makadia and Siegel 2011). The ratio of LA to GA influences degradation and polymers with a higher amount of the more hydrophilic GA generally degrade faster. The degradation products of PLGA are the hydrolysis products LA and GA. Both can enter the citric acid cycle and can be excreted as water and carbon dioxide, or in the case of GA, mainly excreted unchanged by the kidney (Makadia and Siegel 2011). Minor toxicities like transient inflammation have been reported for some PLGA based implants (Athanasiou, Niederauer, and Agrawal 1996), but they likely reflect increased exposure times and reduced clearance of the degradation products.

Injectable, drug loaded polymeric pastes are attractive for local drug delivery because ultrasound or MRI-guided systems allow pinpoint accuracy in directing a needle or catheter system to a target area. Others have described injectable liquids (e.g., Atrigel™) (Dunn 2002) composed of an organic solvent like acetone or polyvinyl-pyrrolidone and a drug that when injected into the body solidified as the solvent dissolved away. Such a system is flawed because introducing an organic solvent into potentially sensitive tissue areas may induce unwanted local toxicity. Local drug delivery systems ranging from drug loaded polymeric coatings of stents, injectable microspheres (Jackson et al. 2007), perivascular films (Jackson et al. 2004) and injectable polymeric pastes have been described (Jackson et al. 2000). In these examples, the antiproliferative drug paclitaxel was used to inhibit proliferative events associated with restenosis, cancer and arthritis. Various polymer formulations for a variety of applications are known in the art (Yu and Ferguson, 2016; Konorty and Hakim, 2014; Pauletti, 2004; and Lughezzani et al. 2012).

An early polymeric paste system described in the literature was based on a blend of polycaprolactone and methoxypolyethylene glycol that was injectable (molten) at above body temperatures, but set to an implant at 37° C. to release drug (Winternitz et al. 1996). The implant was brittle, hard and the high temperature delivery was inappropriate for the injection into sensitive locations. Injectable paclitaxel-loaded polymeric paste made from a mixture of a triblock copolymer and methoxypolyethylene glycol that was injectable at room temperature and formed a solid implant in vivo has also been described (Jackson et al. 2000). This paste performed poorly, in so far as the release rate of the drug paclitaxel and other hydrophobic drugs was too slow to achieve adequate tissue levels of active drug, and the degradation profile of the polymer was too long potentially interfering with re-treatment injections. The inclusion of diblock copolymers of various compositions in solid (not paste) microspheres has been previously described (Jackson et al. 2007). In this case, the dissolution of the diblock from the microspheres allowed for increased hydrophobic drug release as well as opening of the matrix to water and enhanced degradation. Microsphere formulations are quite different to pastes. They do not flow under injection so must be injected in a liquid suspension. As such, they can disperse easily from a targeted tissue area.

SUMMARY OF THE INVENTION

This invention relates to improved polymeric pastes for controlled drug delivery to a mucous membrane. The compositions described herein allow for the formulation and injection of a low viscosity composition into the body of a subject whereby the composition is capable of coating the mucosal surface at a localized site and remaining at the site for a prolonged period of time following initial injection to the site. In one aspect, the present invention provides for delayed drug release from polymeric coating delivery system by using selected polyethylene glycol (PEG) compositions, selected water insoluble polymers and selected mucoadhesive polymers to adjust the properties of the polymer formulation and regulate release rates of drug(s) payload and in situ residence time. The polymer composition may be manufactured from simple polymers that form an injectable polymeric, mucoadhesive composition, which may release the drug and/or drug combinations in a controlled manner. This invention is based on the surprising discovery that only defined ratios and compositions of polyethylene glycol (PEG), a water insoluble polymer and a mucoadhesive polymer can be used to effectively form a mucoadhesive and injectable drug delivery system for in vivo delivery. The compositions described herein are low viscosity and become a gel only after application to an aqueous environment (for example, which allows it to be injected into difficult to access areas). Compositions described herein may be injected through long catheter lines without extra devices and certain compositions described herein may be delivered for embolic purposes.

In a first aspect, there is provided a composition, the composition including: a polyethylene glycol (PEG) composition that is between about 85% and about 96% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2,000 Da; a water insoluble polymer that is between about 2% and about 10% by weight; and a mucoadhesive polymer that is between about 2% and about 5% by weight.

In a further aspect, there is provided a composition, the composition including: a polyethylene glycol (PEG) composition that is between about 85% and about 96% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2,000 Da; a water insoluble polymer that is between about 2% and about 10% by weight; and a mucoadhesive polymer that is between about 2% and about 5% by weight and has a molecular weight 50 kDa.

In a first aspect, there is provided a composition, the composition including: a polyethylene glycol (PEG) composition that is between about 85% and about 99% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2,000 Da; a water insoluble polymer that is between about 2% and about 10% by weight; and a mucoadhesive polymer that is between about 2% and about 5% by weight.

In a further aspect, there is provided a composition, the composition including: a polyethylene glycol (PEG) composition that is between about 85% and about 99% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2,000 Da; a water insoluble polymer that is between about 2% and about 10% by weight; and a mucoadhesive polymer that is between about 2% and about 5% by weight and has a molecular weight 50 kDa.

In a further aspect, there is provided a composition, the composition including: a polyethylene glycol (PEG) composition that is between about 85% and about 96% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 kDa and about 2,000 Da; and an undissolved mucoadhesive polymer that is between about 4% and about 15% by weight. The composition may further include a water insoluble polymer. Alternatively, the a water insoluble polymer may be between about 2% and about 10% by weight; and an undissolved mucoadhesive polymer that is between about 2% and about 5% by weight. The mucoadhesive polymer may have a molecular weight 50 kDa.

In a further aspect, there is provided a composition, the composition including: a polyethylene glycol (PEG) composition that is between about 85% and about 99% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 kDa and about 2,000 Da; and an undissolved mucoadhesive polymer that is between about 4% and about 15% by weight. The composition may further include a water insoluble polymer. Alternatively, the a water insoluble polymer may be between about 2% and about 10% by weight; and an undissolved mucoadhesive polymer that is between about 2% and about 5% by weight. The mucoadhesive polymer may have a molecular weight 50 kDa.

In a further aspect, there is provided a composition, the composition including: a polyethylene glycol (PEG) composition that is between about 85% and about 99% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2,000 Da; and a mucoadhesive polymer that is between about 1% and about 15% by weight and has a molecular weight 50 kDa. The composition may further include a water insoluble polymer. Alternatively, the composition may have a polyethylene glycol (PEG) composition that is between about 85% and about 96% by weight. Alternatively, the composition may have a mucoadhesive polymer that is between about 4% and about 15% by weight and has a molecular weight 50 kDa.

In a further aspect, there is provided a composition, the composition including: a polyethylene glycol (PEG) composition that is between about 85% and about 96% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2 kDa; and an undissolved mucoadhesive polymer that is between about 4% and about 15% by weight and has a molecular weight 50 kDa. The composition may further include a water insoluble polymer.

In a further aspect, there is provided a composition, the composition including: a polyethylene glycol (PEG) composition that is between about 85% and about 96% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2 kDa; and an undissolved mucoadhesive polymer that is between about 4% and about 15%. The composition may further include a water insoluble polymer.

In a further aspect, there is provided a non-aqueous polymeric composition, the composition including: (i) low molecular weight (under 500 Da) polyethylene glycol (PEG) or propylene glycol with (ii) a higher molecular weight (500-2,000) PEG, and (iii) suspended hyaluronic acid. The composition may further include a water insoluble polymer.

In a further aspect, there is provided a non-aqueous polymeric composition, the composition including: (i) low molecular weight (under 500 Da) polyethylene glycol (PEG) or propylene glycol with (ii) a higher molecular weight (500-2000) PEG, (iii) suspended hyaluronic acid and (iiii) a small molecule drug where the composition is injectable through 18 gauge needle under hand pressure.

In a further aspect, there is provided a use of a composition described herein, for the manufacture of a medicament.

In a further aspect, there is provided a use of a composition described herein, for the treatment of a medical condition for which the drug is used.

In a further aspect, there is provided a use of a composition described herein, for the treatment of a mucosal surface area that would benefit from localized drug delivery.

In a further aspect, there is provided a method of administering a drug to a mucosal surface area, the method including: (a) combining the composition described herein with a drug to form a drug loaded composition, and (b) delivering the drug loaded composition to the mucosal surface area.

In a further aspect, there is provided a composition described herein, for use in the treatment of a medical condition.

In a further aspect, there is provided commercial package including: (a) composition described herein; and (b) instructions for the use.

A pharmaceutical composition described herein may be combined together with a pharmaceutically acceptable diluent or carrier.

The second low molecular weight PEG may comprise up to 20% by weight of the composition. The second low molecular weight PEG may comprise between about 5% to about 20% by weight of the composition. The second low molecular weight PEG may comprise between about 2% to about 25% by weight of the composition. The second low molecular weight PEG may comprise between about 1% to about 30% by weight of the composition.

The water insoluble polymer may be selected from one or more of: poly lactic-co-glycolic acid (PLGA), poly(ε-caprolactone) (PCL), polylactic acid (PLA). The water insoluble polymer may be PLGA. Alternatively, the water insoluble polymer may be a co-polymer of acrylic and methacrylic acid esters. The molar ratio of the monomers of lactic acid to glycolic acid may be between 90:10 and 50:50.

The mucoadhesive polymer may be selected from one or more of the following: hyaluronic acid; poly(acrylic acid) and poly(methacrylic acid) derivatives; cyanoacrylates; poly(acrylic acid); carbomer; sodium carboxymethylcellulose (CMC); hydroxypropylcellulose; polycarbophil; chitosan; alginate; gellan; xanthan; thiolated poly(acrylic acid); poloxamer; celluloseacetophthalate; ethylcellulose; methyl cellulose; hydroxy ethyl cellulose; poly(amidoamine) dendrimers; poly(dimethyl siloxane); and poly(vinyl pyrrolidone). The mucoadhesive polymer may be selected from one or more of the following: hyaluronic acid; poly(acrylic acid); carbomer; sodium carboxymethylcellulose; alginic acid. The mucoadhesive polymer may be hyaluronic acid. Alternatively, the mucoadhesive polymer, may be selected from one or more of the following: hyaluronic acid; poly (acrylic acid) and poly(methacrylic acid) derivatives; cyanoacrylates; poly(acrylic acid); carbomer; sodium carboxymethylcellulose (CMC); hydroxypropylcellulose; polycarbophil; thiolated poly(acrylic acid); poloxamer; celluloseacetophthalate; ethylcellulose; methyl cellulose; hydroxy ethyl cellulose; poly(amidoamine) dendrimers; poly(dimethyl siloxane); and poly(vinyl pyrrolidone).

The first low molecular weight PEG may be selected from one of the following approximate molecular weights: PEG 200; PEG 300; PEG 400; and PEG 500. The first low molecular weight PEG may be selected from one of the following: PEG 100; PEG 200; PEG 300; PEG 400; and PEG 500. The second low molecular weight PEG is selected from one of the following approximate molecular weights: PEG 500; PEG 600; PEG 700; PEG 800; PEG 900; PEG 1000; PEG 1100; PEG 1200; PEG 1300; PEG 1400; PEG 1450; PEG 1500; PEG 1600; PEG 1700; PEG 1800; PEG 1900; and PEG 2000. The second low molecular weight PEG is selected from one of the following: PEG 500; PEG 600; PEG 700; PEG 800; PEG 900; PEG 1000; PEG 1100; PEG 1200; PEG 1300; PEG 1400; PEG 1500; PEG 1600; PEG 1700; PEG 1800; and PEG 1900. The second low molecular weight PEG is selected from one of the following: PEG 500; PEG 600; PEG 700; PEG 800; PEG 900; PEG 1000; PEG 1100; PEG 1200; PEG 1300; PEG 1400; PEG 1500; PEG 1600; PEG 1700; and PEG 1800. The second low molecular weight PEG is selected from one of the following: PEG 500; PEG 600; PEG 700; PEG 800; PEG 900; PEG 1000; PEG 1100; PEG 1200; PEG 1300; PEG 1400; PEG 1500; PEG 1600; and PEG 1700. The second low molecular weight PEG is selected from one of the following: PEG 500; PEG 600; PEG 700; PEG 800; PEG 900; PEG 1000; PEG 1100; PEG 1200; PEG 1300; PEG 1400; PEG 1500; and PEG 1600. The second low molecular weight PEG is selected from one of the following: PEG 500; PEG 600; PEG 700; PEG 800; PEG 900; PEG 1000; PEG 1100; PEG 1200; PEG 1300; PEG 1400; and PEG 1500. The PEG may have an average molecular weight between about 200 Da and about 2,000 Da.

The composition may further include one or more low molecular weight PEG polymers selected from one or more of the following: PEG 200; PEG 300; PEG 400; PEG 500; PEG 600; PEG 700; PEG 800; PEG 900; PEG 1000; PEG 1100; PEG 1200; PEG 1300; PEG 1400; PEG 1500; PEG 1600; PEG 1700; PEG 1800; PEG 1900; and PEG 2000.

The composition may further include one or more drug compounds or pharmaceutically acceptable salt, solvate or solvate of the salt thereof. The one or more drug compounds or pharmaceutically acceptable salt, solvate or solvate of the salt thereof may be selected from one or more of the following categories: anti-cancer drugs; anti-inflammatory agents; anti-bacterial drugs; anti-viral drugs; anti-fungal drugs; anti-proliferative drugs; anti-fibrotic drugs; anti-restenotic drugs (sirolimus-based drugs and taxane-based drugs); anesthetic drugs; neuromodulatory drugs; and analgesics.

The one or more drug compounds or pharmaceutically acceptable salt, solvate or solvate of the salt thereof may be an anti-cancer drug selected from one or more of the following: Actinomycin; All-trans Retinoic Acid; Azacitidine; Azathioprine; Bleomycin; Bortezomib; Carboplatin; Capecitabine; Cisplatin; Chlorambucil; Cyclophosphamide; Cytarabine; Daunorubicin; Docetaxel; Doxifluridine; Doxorubicin; Epirubicin; Epothilone; Etoposide; Fluorouracil; Gemcitabine; Hydroxyurea; Idarubicin; Imatinib; Irinotecan; Mechlorethamine; Mercaptopurine; Methotrexate; Mitoxantrone; Oxaliplatin; Paclitaxel; Pemetrexed; Teniposide; Tioguanine; Topotecan; Valrubicin; Vemurafenib; Vinblastine; Vincristine; Vindesine; and Vinorelbine. The drug may be selected from one or more of: Gemcitabine HCl, gemcitabine, mitomycin, docetaxel, and paclitaxel. The one or more drug compounds or pharmaceutically acceptable salt, solvate or solvate of the salt thereof may be an anesthetic drug and the anesthetic may be a local anesthetic selected from one or more of the following: Procaine; Benzocaine; Chloroprocaine; Cocaine; Cyclomethycaine; Dimethocaine/Larocaine; Piperocaine; Propoxycaine; Procaine/Novocaine; Proparacaine; Tetracaine/Amethocaine; Articaine; Bupivacaine; Cinchocaine/Dibucaine; Etidocaine; Levobupivacaine; Lidocaine/Lignocaine/Xylocaine; Mepivacaine; Prilocaine; Ropivacaine; and Trimecaine.

The one or more drug compounds or pharmaceutically acceptable salt, solvate or solvate of the salt thereof may be an antibiotic medication, which may include penicillins, cephalosporins, polymyxins, rifamycins, lipiarmycins, quinolones, sulfonamides, macrolides, lincosamides, tetracyclines, aminoglycosides, lipopeptides, glycylcyclines, oxazolidinones, and lipiarmycins, cephalexin, cefazolin, gentamicin, ciprofloxacin, clindamycin, macrodantin, tobramycin, rifampicin, daptomycin, linezolid, vancomycin, fusidic acid, silver compounds, cannabinoids and others. An antibiotic drug may also include silver and a cannabinoid.

The one or more drug compounds or pharmaceutically acceptable salt, solvate or solvate of the salt thereof may be an anti-fungal drug, such as polyenes, azoles, triazoles, antimetabolites, allylamines, echinocandins. Anti-fungal drugs may include, for example, but are not limited to amphotericin B, nystatin, clotrimazole, econazole, miconazole, fluconazole, terbinafine, fluconazole, ketoconazole, caspofungin, tolnaftate, ivermectin, flucytosine, griseofulvin.

The mucosal surface area may be selected from one or more of the following: urogenital tract; gastrointestinal tract; and respiratory tract. The mucosal surface area may be selected from one or more of the following: kidney; ureter; bladder; urethra; uterus; vagina; penis; mouth; esophagus; stomach; small intestine; large intestine; rectum; anus; nasal sinuses; pharynx; larynx; trachea; bronchi; bronchioles; lungs. The medical condition may be selected from one or more of: cancer; wound; and inflammation. The drug loaded composition may be for the treatment of one or more of: cancer; wound; and inflammation.

The composition may further include a water insoluble polymer may be selected from one or more of: poly lactic-co-glycolic acid (PLGA); poly(ε-caprolactone) (PCL); and polylactic acid (PLA). The water insoluble polymer may be PLGA. Alternatively, the water insoluble polymer may be PCL or PLA. Alternatively, the water insoluble polymer may be a co-polymer of acrylic and methacrylic acid esters. The molar ratio of the monomers of lactic acid to glycolic acid may be between 90:10 and 50:50. The water insoluble polymer may be between 2% and 20% by weight of the composition. The water insoluble polymer may be between 2% and 15% by weight of the composition. The water insoluble polymer may be up to 20% by weight of the composition. The water insoluble polymer may be up to 15% by weight of the composition. The PLGA may be between 2% and 20% by weight of the composition. The PLGA may be between 2% and 15% by weight of the composition. The PLGA may be up to 20% by weight of the composition. The PLGA may be up to 15% by weight of the composition.

Methods are provided for using the aforementioned compositions to form implants in vitro and in vivo. In vivo methodologies include injection of the composition to a site in a subject's body where the drug-containing implant may be formed. Also provided are injection devices containing the composition described herein.

DETAILED DESCRIPTION OF THE INVENTION

Described herein is a new formulation that adheres to the renal pelvis and ureter or other mucous membrane to deliver the chemotherapeutic agent (for example, gemcitabine) locally and we herein evaluate the feasibility, safety and pharmacokinetic properties of an injectable mucoadhesive polymer composition.

Previous pastes were 50/50 PEG 300/PLGA with 10% gemcitabine and 2% Sodium hyaluronate in 69/31 PEG300/PLGA paste with 5% gemcitabine. Pastes were safe (mild hydronephrosis in some pigs) and the systemic concentration of gemcitabine was low. Several improvements were made to the paste to create a gemcitabine composition that is easily injectable and shows some pelvis adherence and no interaction with the urinary catheter.

A gemcitabine paste composition as described herein has a lowered PLGA content, more hyaluronic acid, a combination of PEGs of different molecular weights and utilizes gemcitabine HCl instead of gemcitabine.

Figure 1:
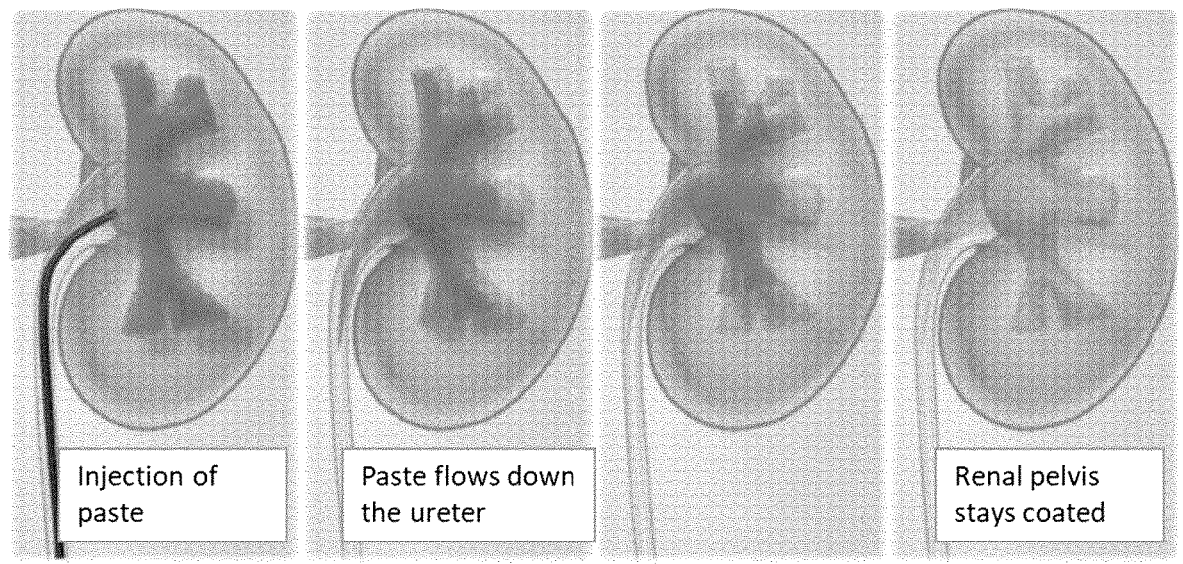
FIG. 1 shows a schematic of gemcitabine paste in the renal pelvis.

The working principle of compositions disclosed herein, is not based on retention through setting, but on gelling and mucoadhesion. A large injection volume of 10 mL can be used to coat the complete renal pelvis (schematic shown in FIG. 1). The paste is injected through a 5 F catheter into the renal pelvis. After at least 5 min, the ureteral catheter was removed and the paste slowly moved down into the bladder without blocking the ureter. Due to the paste's mucoadhesive properties, the renal pelvis remains coated with paste and the release of gemcitabine into the tissue was sustained.

In embodiments of the invention, water-insoluble polymers may be used to control the consistency of biocompatible polymer pastes and subsequent release of a variety of drugs therefrom.

For polymers where the viscosity cannot be directly measured (e.g., PLGA—waxy chunks), the polymer is dissolved in an appropriate solvent and the relative viscosity is calculated by dividing the viscosity of the polymer solution by the viscosity of pure solvent. The majority of polymers show a distinct relation between molar mass and viscosity and as a rule, the viscosity of polymer solutions increases with increasing molar mass. The inherent viscosity (IV) is the ratio of the natural logarithm of the relative viscosity to the mass concentration of the polymer and is provided as a measure of molecular size and is typically reported in deciliters per gram (dL/g). IV is simple and inexpensive to obtain and reproducible. Gel Permeation Chromatography (GPC) may be used as a chromatographic method for measuring molecular size. The molecular size can be expressed as molecular weight (MW) in Daltons obtained from calibration with a standard polymer (for example, polystyrene standards in chloroform). The molecular weight of styrene is 104 Daltons and standards of known polystyrene are readily available. MWs obtained by GPC are very method-dependent and may be less reproducible between laboratories. Alternatively, molecular weight may be measured by size exclusion chromatography (SEC), high temperature gel permeation chromatography (HT-GPC) or mass spectrometry (MALDI TOF-MS).

A water-insoluble polymers may be a polyester. The water-insoluble polymer may be a polylactic-co-glycolic acid (PLGA), wherein, the ratio of LA:GA is equal to or below 75:25. The ratio of LA:GA may be about 50:50. Durect Corporation™ who supplied the PLGA used in these experiments graph inherent viscosity (IV) in dL/g in hexafluoroisopropanol (HFIP) against molecular weight in Daltons for their 50:50 and 65:35 LA:GA polymers. Similarly, when Durect™ calculated the IV values in dL/g for 75:25 PLGA and 85:15 PLGA, chloroform, was used as the solvent. The relationship between IV and molecular weight in Daltons is different depending on the ratio of LA:GA. As described herein an inherent viscosity of between 0.15 to 0.25 dL/g is an optional range, but an IV in the range 0.25-0.5 dL/g would also be suitable. Alternatively, the range may be between about 0.15 dL/g and about 0.5 dL/g.

Using a 50:50 PLGA a range of 0.15 to 0.25 dL/g is approximately equivalent to a range of about 4,300 Da to about 6,700 Da and a range of 0.25 to 0.5 dL/g is approximately equivalent to a range of about 6,700 Da to about 26,600 Da. Using a 65:35 PLGA a range of 0.15 to 0.25 dL/g is approximately equivalent to a range of about 6,500 Da to about 14,200 Da and a range of 0.25 to 0.5 dL/g is approximately equivalent to a range of about 14,200 Da to about 39,000 Da. The broader range of 0.15 to 0.5 dL/g is equivalent to about 4,300 Da to about 26,600 Da for 50:50 PLGA and about 6,500 Da to about 39,000 Da for 65:35 PLGA. Accordingly, the range for PLGA may be anywhere between 4,300 Da and about 39,000 Da. Alternatively, the range for PLGA may be anywhere between 4,300 and about 40,000 or higher if using 75:25 (i.e. up to a molecular weight of 56,500 Da). For the 50:50, 65:35 and 75:25 LA:GA polymers, an IV of 0.5 g/dL approximately corresponds to molecular weights of 26,600, 39,000, and 56,500. As tested the Durect™ 50:50 having an IV of 0.25 dL/g is about 6,700 Da, Durect™ 75:25 having an IV of 0.47 dL/g is about 55,000 Da and Durect™ 85:15 having an IV of 0.55 dL/g to 0.75 dL/g is in the range of about 76,000 Da to about 117,000 Da.

Of particular interest are PLGA pastes having a ratio of LA:GA of 50:50 with an IV of between 0.15 dL/g to 0.25 dL/g (i.e. molecular weights of between 4,300 Da to 6,700 Da). However, PLGA pastes having a ratio of LA:GA of 50:50 with an IV of 0.25 dL/g to 0.5 dL/g (i.e. a molecular weight of about 6,700 Da to about 26,600 Da) are also useful.

The PLGA polymer molecular weight may be reported as inherent viscosity (IV). The IV may be 0.15-0.5 dL/g. The PLGA polymer IV may be <0.3 dL/g. The IV may lie between 0.15-0.25 dL/g. Low molecular weight versions of PLGA with a 50:50 ratio of LA:GA and an inherent viscosity under 0.3 dL/g may be rendered fully miscible with a low molecular weight biocompatible glycol using mild heating to form either a viscous or fluid paste at room temperature.

Drug delivery compositions described herein may exist in a variety of "paste" forms. Examples of paste forms may include liquid paste or paste, depending on to polymers used, the amount of the polymers used and the temperature.

Drug delivery compositions described herein may release one or more drugs over a period of several hours or over several months, depending on the need. Compositions described herein may be used for localized delivery of one or more drugs to a subject. Examples of drugs that may be delivered using these compositions are not limited, and may include anti-cancer drugs; anti-inflammatory agents; anti-bacterial drugs; anti-viral drugs; anti-fungal drugs; anti-proliferative drugs; anti-fibrotic drugs; anti-restenotic drugs (sirolimus-based drugs and taxane-based drugs); anesthetic drugs; neuromodulatory drugs; and analgesics, depending on the condition or conditions being treated or ameliorated. Further examples are drugs for the treatment of neurological conditions, drugs to treat gastro-intestinal conditions like diverticulosis and alimentary ulcers. The compositions described herein are suitable for any drug that would benefit from adherence to a mucosal tissue surface and/or prolonged release from a paste implant.

Examples of anti-cancer drugs that may be used with the compositions of the present invention include docetaxel, paclitaxel, mitomycin, cisplatin, etoposide, vinca alkaloid drugs, doxorubicin drugs, rapamycin, camptothecins, gemcitabine, finasteride (or other cytotoxics); bicalutamide, enzalutamide, ivermectin, tamoxifen, sunitinib, erlotinib. Anti-cancer biological agents may also be used in the formulation such as antibody based therapies e.g. herceptin, avastin, erbitux or radiolabelled antibodies or targeted radiotherapies such as PSMA-radioligands.

Anti-inflammatory agents may include acetaminophen and non-steroidal drugs like ibuprofen, acetylsalicylic acid, naproxen, diclofenac, meloxicam, as well as steroids like prednisone and others.

Local analgesia or local anesthetic medications may include, for example, one or more of the following: Procaine; Benzocaine; Chloroprocaine; Cocaine; Cyclomethycaine; Dimethocaine/Larocaine; Piperocaine; Propoxycaine; Procaine/Novocaine; Proparacaine; Tetracaine/Amethocaine, Articaine; Bupivacaine; Cinchocaine/Dibucaine; Etidocaine; Levobupivacaine; Lidocaine/Lignocaine/Xylocaine; Mepivacaine; Prilocaine; Ropivacaine; and Trimecaine.

Antibiotic medications may include penicillins, cephalosporins, polymyxins, rifamycins, lipiarmycins, quinolones, sulfonamides, macrolides, lincosamides, tetracyclines, aminoglycosides, lipopeptides, glycylcyclines, oxazolidinones, and lipiarmycins, cephalexin, cefazolin, gentamicin, ciprofloxacin, clindamycin, macrodantin, tobramycin, rifampicin, daptomycin, linezolid, vancomycin, fusidic acid silver compounds, cannabinoids and others.

Examples of anti-fungal drugs are polyenes, azoles, triazoles, antimetabolites, allylamines, echinocandins. Anti-fungal drugs may include, for example, but are not limited to amphotericin B, nystatin, clotrimazole, econazole, miconazole, fluconazole, terbinafine, fluconazole, ketoconazole, caspofungin, tolnaftate, ivermectin, flucytosine, and griseofulvin.

The drugs may be hydrophobic or may be hydrophilic. Specific drugs may be selected from one of more of the following: docetaxel; ivermectin; bicalutamide; cephalexin; sunitinib; tamsulosin; desoximetasone; gemcitabine; rapamycin; and ibuprofen.

Drug delivery compositions may be prepared and utilized to treat or prevent a variety of diseases or conditions, particularly where the treatment site is at or near a mucosal tissue. Examples of diseases or conditions that may be treated, may for example, include cancer, pain, inflammatory conditions, fibrotic conditions, benign tumors (including benign prostate hyperplasia), and infections. For example, the compositions described herein may be used to treat the renal pelvis as described above. The paste might be applied to any mucosal surface or moist tissue area for localized drug delivery. Of particular importance might be to treat the inside of the GI tract such as to treat cancer, wounds (e.g., ulcer) or inflammation (e.g., inflammatory bowel diseases: ulcerative colitis, Crohn disease). Also the paste might be applied with drugs to treat or fill inflamed diverticula. Diseases of the mouth, vagina and rectal areas might be treated. The localized application of hyaluronic acid is used to prevent surgical adhesions so an improvement might be to use this paste and include and antiadhesive drug. Wounds and post-operative pain might be suitable indications.

As used herein, "mucosal tissue" or "mucous membrane" or "mucosa" as used herein refers to a membrane that lines various cavities in the body (i.e. urogenital tract; gastrointestinal tract; and respiratory tract) and covers the surface of internal organs. The mucous membrane consists of one or more layers of epithelial cells overlying connective tissue. The urogenital tract includes the kidney, ureter, bladder, urethra, uterus, vagina and penis. The gastrointestinal tract (GI tract) includes the mouth, esophagus, stomach, small intestine, large intestine, rectum and anus. The respiratory tract includes the mouth, nasal sinuses, pharynx, larynx, trachea, bronchi, bronchioles, lungs.

As used herein a "mucoadhesive polymer" refers to any polymer that has properties that cause the polymer to adhere to a mucosal surface. Such polymers are preferably biocompatible. Mucoadhesive polymers may be selected from one or more of the following: hyaluronic acid (HA); poly(acrylic acid) and poly(methacrylic acid) derivatives; cyanoacrylates; poly(acrylic acid) (carbomer); sodium carboxymethylcellulose (CMC); hydroxypropylcellulose; polycarbophil; chitosan; alginate; gellan; thiolated poly(acrylic acid); poloxamer; celluloseacetophthalate; ethylcellulose; methyl cellulose; hydroxy ethyl cellulose; poly(amidoamine) dendrimers; poly(dimethyl siloxane); and poly(vinyl pyrrolidone) (Roy et al. 2009). Generally HA is not used in a non-aqueous setting as a dispersion, as described herein. Also, compositions described herein have PEGs in a ratio so that the HA does not settle at a certain temperature. Alternatively, mucoadhesive polymers may be selected from one or more of the following: hyaluronic acid; poly(acrylic acid) and poly(methacrylic acid) derivatives; cyanoacrylates; poly (acrylic acid) (carbomer); sodium carboxymethylcellulose; hydroxypropylcellulose; polycarbophil; chitosan; alginate; gellan; thiolated poly(acrylic acid); poloxamer; celluloseacetophthalate; ethylcellulose; methyl cellulose; hydroxy ethyl cellulose; poly(amidoamine) dendrimers; poly(dimethyl siloxane); and poly(vinyl pyrrolidone).

Furthermore, as described herein PEGs are combined to tailor the formulation for the specific administration (e.g., long catheter lines) and stability (e.g., storage, no sedimentation) and disintegration properties, as higher MW PEGs are less water soluble.

As used herein a "water insoluble polymer" refers to any polymer that is insoluble in water. Such polymers are preferably biocompatible. Water insoluble polymers may be selected from one or more of: poly lactic-co-glycolic acid (PLGA); poly(ε-caprolactone) (PCL); and polylactic acid (PLA). Alternatively, the water insoluble polymer may be a co-polymer of acrylic and methacrylic acid esters.

As used herein, "poly lactic-co-glycolic acid" (PLGA) is a copolymer of lactic acid and glycolic acid having the structure

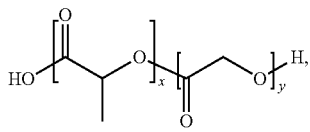

wherein the "x" represents the number of lactic acid (lactide) subunits and the y represents the number of glycolic acid (glycolide) subunits. Depending on the ratio of lactide to glycolide used for the polymerization, different forms of PLGA can be obtained: these are usually identified in regard to the molar ratio of the monomers used (for example, PLGA 75:25 identifies a copolymer whose composition is 75% lactic acid and 25% glycolic acid). Suitable molar ratios may be anywhere between 90:10 and 50:50. Generally, the ratio can dictate the degradation of the PLGA. For example, PLGA 50:50 shows fast degradation rate that (for example, 2 months), while PLGA 75:25 takes longer (for example, 5 months), and PLGA 85:15 can take longer still (for example, 6 months) for complete degradation.

Where used the PLGA may be between 2% and about 20% by weight. An IV for PLGA 50/50 is about 0.15 dL/g, but an IV of 0.25 dL/g for 65/35 PLGA would also be useful. A useful IV range of 0.1 dL/g to 0.3 dL/g for the PLGA would be suitable. The molar ratio of the monomers of lactic acid to glycolic acid may be between about 90:10 and about 50:50.

As used herein, "polyethylene glycol" (PEG) or polyethylene oxide or polyoxyethylene, depending on its molecular weight, is a polyether compound having the structure

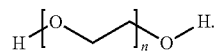

As used herein there is a first low molecular weight PEG that may be selected from one of the following: PEG 100; PEG 200; PEG 300; PEG 400; and PEG 500. There is also a second low molecular weight PEG is selected from one of the following: PEG 100; PEG 200; PEG 300; PEG 400; PEG 500; PEG 600; PEG 700; PEG 800; PEG 900; PEG 1000; PEG 1100; PEG 1200; PEG 1300; PEG 1400; PEG 1500; PEG 1600; PEG 1700; PEG 1800; PEG 1900; and PEG 2000. The PEG composition, as described herein may also further include one or more low molecular weight PEG selected from one or more of the following: PEG 100; PEG 200; PEG 300; PEG 400; PEG 500; PEG 600; PEG 700; PEG 800; PEG 900; PEG 1000; PEG 1100; PEG 1200; PEG 1300; PEG 1400; PEG 1500; PEG 1600; PEG 1700; PEG 1800; PEG 1900; and PEG 2000. The PEG polymers as used herein may have an average molecular weight between about 100 Da and about 2,000 Da. The PEG polymers as used herein may have an average molecular weight between about 200 Da and about 2,000 Da.

The polyethylene glycol (PEG) as used herein may be selected from: PEG 100; PEG 200; PEG 300; PEG 400; PEG 500; PEG 600; PEG 700; PEG 800; PEG 900; PEG 1000; PEG 1100; PEG 1200; PEG 1300; PEG 1400; PEG 1500; PEG 1600; PEG 1700; PEG 1800; PEG 1900; and PEG 2000. The polyethylene glycol (PEG) may have an average molecular weight between about 100 Da and about 1,450 Da. The polyethylene glycol (PEG) may have an average molecular weight between about 100 Da and about 2,000 Da. The polyethylene glycol (PEG) may have a molecular weight between about 300 Da and about 1,450 Da. The polyethylene glycol (PEG) may have a molecular weight between about 300 Da and about 500 Da and a molecular weight between about 500 Da and about 2000 Da.

Alternatively, instead of PEG, suitable compositions might comprise a propylene glycol or glycerol may be used or may be used in combination with PEG.

Local anesthetics usually fall into one of two classes: aminoamide and aminoester. Most local anesthetics have the suffix "-caine". The local anesthetics in the aminoester group may be selected from one or more of the following: Procaine; Benzocaine; Chloroprocaine; Cocaine; Cyclomethycaine; Dimethocaine/Larocaine; Piperocaine; Propoxycaine; Procaine/Novocaine; Proparacaine and Tetracaine/Amethocaine. The local anesthetics in the aminoamide group may be selected from one or more of the following: Articaine; Bupivacaine; Cinchocaine/Dibucaine; Etidocaine; Levobupivacaine; Lidocaine/Lignocaine/Xylocaine; Mepivacaine; Prilocaine; Ropivacaine; and Trimecaine. Local anesthetics may also be combined (for example, Lidocaine/prilocaine or Lidocaine/tetracaine).

Furthermore, local anesthetics used for injection may be mixed with vasoconstrictors to increase residence time, and the maximum doses of local anesthetics may be higher when used in combination with a vasoconstrictor (for example, prilocaine hydrochloride and epinephrine; lidocaine, bupivacaine, and epinephrine; lidocaine and epinephrine; or articaine and epinephrine).

Anti-cancer drugs as may be used in the composition described herein, may be categorized as alkylating agents (bi and mono-functional), anthracyclines, cytoskeletal disruptors, epothilone, topoisomerase inhibitors (I and II), kinase inhibitors, nucleotide analogs and precursor analogs, peptide antibiotics, platinum-based agents, vinca alkaloids, and retinoids. Alkylating agents, may be bifunctional alkylators (for example, Cyclophosphamide, Mechlorethamine, Chlorambucil and Melphalan) or monofunctional alkylators (for example, Dacarbazine (DTIC), Nitrosoureas and Temozolomide). Examples of anthracyclines are Daunorubicin, Doxorubicin, Epirubicin, Idarubicin, Mitoxantrone, and Valrubicin. Cytoskeletal disruptors or taxanes are Paclitaxel, Docetaxel, Abraxane and Taxotere. Epothilones may be epothilone or related analogs. Histone deacetylase inhibitors may be Vorinostat or Romidepsin. Inhibitors of topoisomerase I may include Irinotecan and Topotecan. Inhibitors of topoisomerase II may include Etoposide, Teniposide or Tafluposide. Kinase inhibitors may be selected from Bortezomib, Erlotinib, Gefitinib, Imatinib, Vemurafenib or Vismodegib. Nucleotide analogs and precursor analogs may be selected from Azacitidine, Azathioprine, Capecitabine, Cytarabine, Doxifluridine, Fluorouracil, Gemcitabine, Hydroxyurea, Mercaptopurine, Methotrexate or Tioguanine/Thioguanine. Peptide antibiotics like Bleomycin or Actinomycin. Platinum-based agents may be selected from Carboplatin, Cisplatin or Oxaliplatin. Retinoids may be Tretinoin, Alitretinoin or Bexarotene. The Vinca alkaloids and derivatives may be selected from Vinblastine, Vincristine, Vindesine and Vinorelbine.

An anti-cancer drug that may be used with the compositions described herein, may be selected from one or more of: Actinomycin; All-trans retinoic acid; Azacitidine; Azathioprine; Bleomycin; Bortezomib; Carboplatin; Capecitabine; Cisplatin; Chlorambucil; Cyclophosphamide; Cytarabine; Daunorubicin; Docetaxel; Doxifluridine; Doxorubicin; Epirubicin; Epothilone; Etoposide; Fluorouracil; Gemcitabine; Hydroxyurea; Idarubicin; Imatinib; Irinotecan; Mechlorethamine; Mercaptopurine; Methotrexate; Mitoxantrone; Oxaliplatin; Paclitaxel; Pemetrexed; Teniposide; Tioguanine; Topotecan; Valrubicin; Vemurafenib; Vinblastine; Vincristine; Vindesine; and Vinorelbine. Alternatively, the anti-cancer drug may be a biological agent and may be selected from Herceptin (Trastuzumab), Ado-trastuzumab, Lapatinib, Neratinib, Pertuzumab, Avastin, Erbitux or radiolabelled antibodies or targeted radiotherapies such as PSMA-radioligands. The anti-cancer drug may be an Androgen Receptor, an Estrogen Receptor, epidermal growth factor receptor (EGFR) antagonists, or tyrosine kinase inhibitor (TKI). An anti-angiogenesis agent may be selected from avastin, an epidermal growth factor receptor (EGFR) antagonists or tyrosine kinase inhibitor (TKI). An Immune modulator such as Bacillus Calmette-Guerin (BCG).

As used herein a "drug" refers to any therapeutic moiety, which includes small molecules and biological agents (for example, proteins, peptides, nucleic acids). Furthermore, a biological agent is meant to include antibodies and antigens. As used herein, the term drug may in certain embodiments include any therapeutic moiety, or a subset of therapeutic moieties. For example, but not limited to one or more of the potentially overlapping subsets and one or more drugs, as follows: hydrophobic drugs, hydrophilic drugs; a cancer therapeutic drug; a local anesthetic drug; an anti-biotic drug; an anti-viral drug; an anti-inflammatory drug; a pain drug; an anti-proliferative drug; an anti-fibrotic drug; or any drug that might benefit from a localized and/or sustained release.

As used herein, "an antibody" is a polypeptide belonging to the immunoglobulin superfamily. In particular, "an antibody" includes an immunoglobulin molecule or an immunologically active fragment of an immunoglobulin molecule (i.e., a molecule(s) that contains an antigen binding site), an immunoglobulin heavy chain (alpha ($\alpha$), mu ($\mu$), delta ($\delta$) or epsilon ($\epsilon$)) or a variable domain thereof (VH domain), an immunoglobulin light chain (kappa ($\kappa$) or lambda ($\lambda$)) or a variable domain thereof (VL domain), or a polynucleotide encoding an immunoglobulin molecule or an immunologically active fragment of the immunoglobulin molecule. Antibodies includes a single chain antibody (e.g., an immunoglobulin light chain or an immunoglobulin heavy chain), a single-domain antibody, an antibody variable fragment (Fv), a single-chain variable fragment (scFv), an scFv-zipper, an scFv-Fc, a disulfide-linked Fv (sdFv), a Fab fragment (e.g., CLVL or CHVH), a F(ab') fragment, monoclonal antibodies, polyclonal antibodies. As used herein "antigen" refers to any epitope-binding fragment and a polynucleotide (DNA or RNA) encoding any of the above.

As used herein, a "paste" is any composition described herein that has the characteristics of a solid and of a liquid depending on applied load and the temperature. Specifically, the viscosity of a paste may be anywhere where it is injectable at room temperature and may be measured by any number of methods known to those of skill in the art. Numerous types of viscometers and rheometers are known in the art. For example rheometers by Anton Paar™, MCR 502 or MCR72.

Methods

Paste Preparation

For example, the base paste recipe for the renal pelvis is given in TABLE 1.

The paste was prepared by weighing the polymers into a glass vial and stirring at 60° C. When the polymers formed a homogenous melt, the mucoadhesive polymer was added. If drug is to be added, it is added following the polymer paste preparation. The values for the paste polymers (i.e. a polyethylene glycol (PEG) composition that is between about 85% and about 96% by weight, comprising (i) a first low molecular weight polyethylene glycol (PEG) and (ii) an optional second low molecular weight polyethylene glycol (PEG) wherein the first low molecular weight PEG and the second low molecular weight PEG have an average molecular weight between about 100 Da and about 1,500 Da; a water insoluble polymer that is between about 2% and about 10% by weight; and a mucoadhesive polymer that is between about 2% and about 5% by weight) is prepared as a total % out of 100% before mixing with drug. When the drug is added the % associated therewith is a percent of the total composition with drug and the "pre-drug paste" component % s are based on their proportions prior to adding the drug. For example, 4% means 4 g of drug in 100 g paste. Drug(s) were incorporated using levigation or a mortar and pestle.

The injectability of a paste will depend on many parameters (i.e. needle size, needle lengths, volume, tissue backpressure, strength of the person administering the paste). Normally it is preferred that a paste be easily drawn up into a syringe using a 18 to 14 gauge needle and easily injected into a tissue zone using an 18 gauge or even smaller needle with a small amount of extra pressure. However, for particular uses and depending on the gauge of the needle, having a more viscous paste (i.e. more difficult to inject), may be desirable. The polymer compositions described herein may be injected through 18 gauge lines under hand pressure.

TABLE 1

Exemplary base paste for injection into the renal pelvis.

| Polymer | Percentage (%) |
|---|---|
| PEG 300 | 78 |
| PEG 1000 | 14 |
| poly lactic-co-glycolic acid (PLGA) | 5 |
| Hyaluronic Acid (HA) (>1800 kDa) | 3 |

Animal Procedures

Paste Injection

Using a retrograde approach, pigs received an injection of the new formulation of gemcitabine into one renal pelvis via cystoscopy and a ureteral catheter. Over 24 hours, urine was collected in three-hour intervals from urinary catheter bags and blood was collected via venous catheters. Ultrasound was performed to monitor urinary tract obstruction.

Sampling

Blood was sampled from venous catheters and collected in serum tubes at 15 min, 1 h, 4 h, 8 h, 12 h, 18, h, 24 h. Blood was stored in the fridge and stabilized with tetrahydrouridine. Urine was collected continuously in 3 h intervals in catheter bags via transurethral catheter until 24 h (0-3 h, 3-6 h, 6-9 h, 9-12 h, 12-15 h, 15-18 h, 18-21 h, 21-24 h). Urine gemcitabine was stabilized with tetrahydrouridine and stored in the fridge until further processing.

Ultrasound and Nephrectomy

Baseline and daily ultrasounds were performed to monitor for hydronephrosis. Kidneys were removed on day 4 after injection of the gemcitabine paste.

Analytical Methods

LCMS/MS for Serum and Urine Sample Analysis

Methods for Liquid Chromatography-Mass Spectrometry (LC-MS) are known in the art for serum and urine analysis.

HPLC/UV for Tissue Extraction Experiment

Instrumentation and Method:

The gemcitabine assay used for the tissue extracts uses the instrumentation and parameters outlined in TABLE 2. A calibration curve ranging from 0.75 to 100 µg/mL was routinely run with the samples of unknown concentration. The calibrators are serially diluted from a 1 mg/mL stock solution of gemcitabine in methanol (containing 1% water) using PBS or a 50% water/methanol mixture.

TABLE 2

HPLC/UV instrumentation and parameters for gemcitabine HCl analysis.

| | |
|---|---|
| Pump | Waters 1525 Binary HPLC Pump |
| Autosampler | Waters 717 Plus Autosampler |
| Column | Waters C-18 ™, Nova-Pak, 4 µm, 3.9 × 150 mm |
| Detector | Waters 2489 ™ UV/Visible Detector |
| Flow Rate | 1 mL/min |
| Column Temperature | Ambient, no temperature control |
| Injection Volume | 20 µL |
| Elution | Isocratic |
| Mobile Phase | 92.5% Ammonium acetate Buffer[1] |
| | 6% Methanol |
| | 1.5% Acetonitrile |
| Retention Time | 2.5 min |
| Wavelength | 254 nm (dual with 220 nm) |
| Diluent of Standards | PBS 7.4 |

[1]Ammonium acetate buffer is ammonium acetate (M = 77 g/moL), 1.542 g/L water, pH at 6.3 adjusted with approximately 3.6 mL phosphoric acid (85%).

Sample Preparation for Tissue Extraction

Gemcitabine was extracted from the tissue samples using a 50/50 mixture of water and methanol, spun and the supernatant directly measured.

Viscosity Measurement

An Anton Parr', MCR72 viscometer was used to determine paste viscosities. A parallel plate 25 mm geometry (Measuring system PP25), a gap size of 0.5 mm and the software RheoCompass 1.20™, was used to determine flow curves using a rotational shear rates between 1-100 1/s at ambient temperature (20-25° C.).

EXAMPLES

Example 1: Serum Data—PK Analysis

Figure 2:
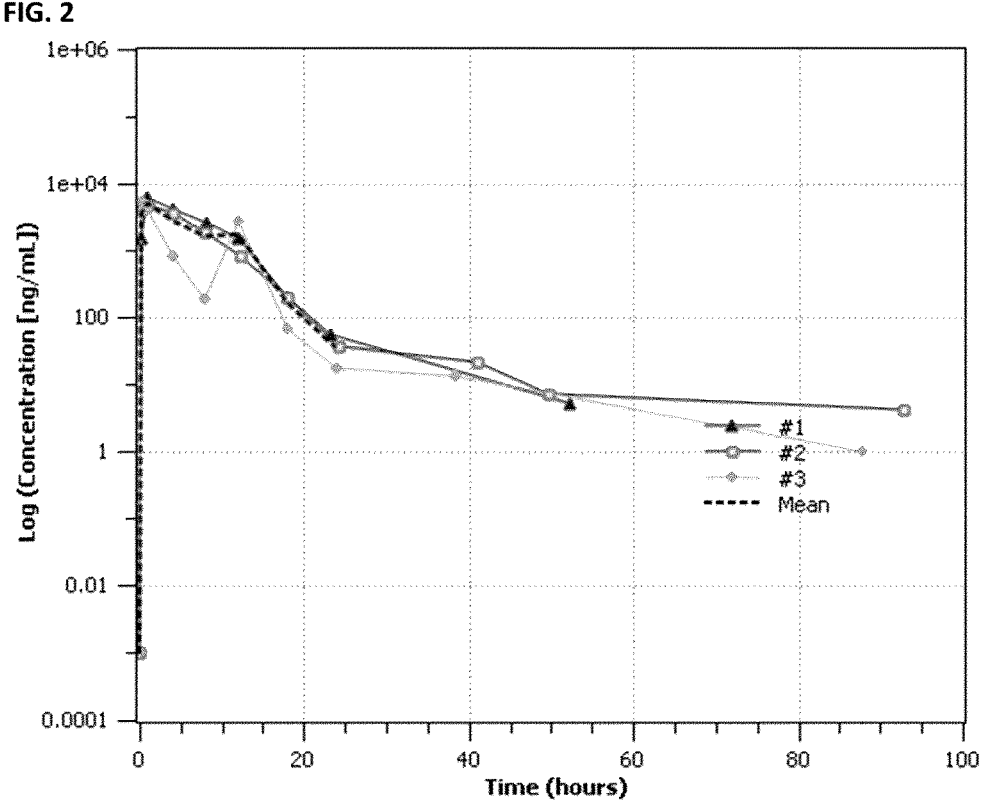
FIG. 2 shows a semi log plot of concentration vs. time data after administration of a gemcitabine paste into the renal pelvis (1000 mg/pig).

To calculate PK parameters for the pig experiment, a non-compartmental analysis was run using Phoenix 64™ (Build 6.3.0.395) WinNonlin 6.3™. Concentration vs. time data is presented in FIG. 2. The pharmacokinetic parameters area under the curve (AUC), area under the first moment curve (AUMC), clearance (Cl/F, for extravascular dosing), maximum observed concentration ($c_{max}$), terminal half-life ($t_{1/2}$), terminal rate constant ($k_{el}$ or $\lambda_z$), mean residence time (MRT) and volume of distribution (V/F, for extravascular dosing) are presented in TABLE 3. The results show that there is retention of paste in the renal pelvis, especially when compared to serum IV data (see further analysis EXAMPLE 4).

TABLE 3

Non-compartmental PK parameters for serum data after injection of a gemcitabine paste into the renal pelvis.

| Parameter | Unit | Value |
|---|---|---|
| $AUC_{0-inf}$ | h · ng/mL | 37838.8 ± 9415.1 |
| $AUMC_{0-inf}$ | h · h · ng/mL | 249543.5 ± 40423.1 |
| Cl/F | mL/h/kg | 727.1 ± 187 |
| $C_{max}$ | ng/mL | 5532.2 ± 771.7 |
| $t_{1/2}$ | h | 4.1 ± 1.4 |
| $k_{el}$ | 1/h | 0.18 ± 0.05 |
| MRT | h | 6.7 ± 0.8 |
| V/F | mL/kg | 4521.6 ± 2549 |

Example 2: Urine Data—PK Analysis

Figure 3:
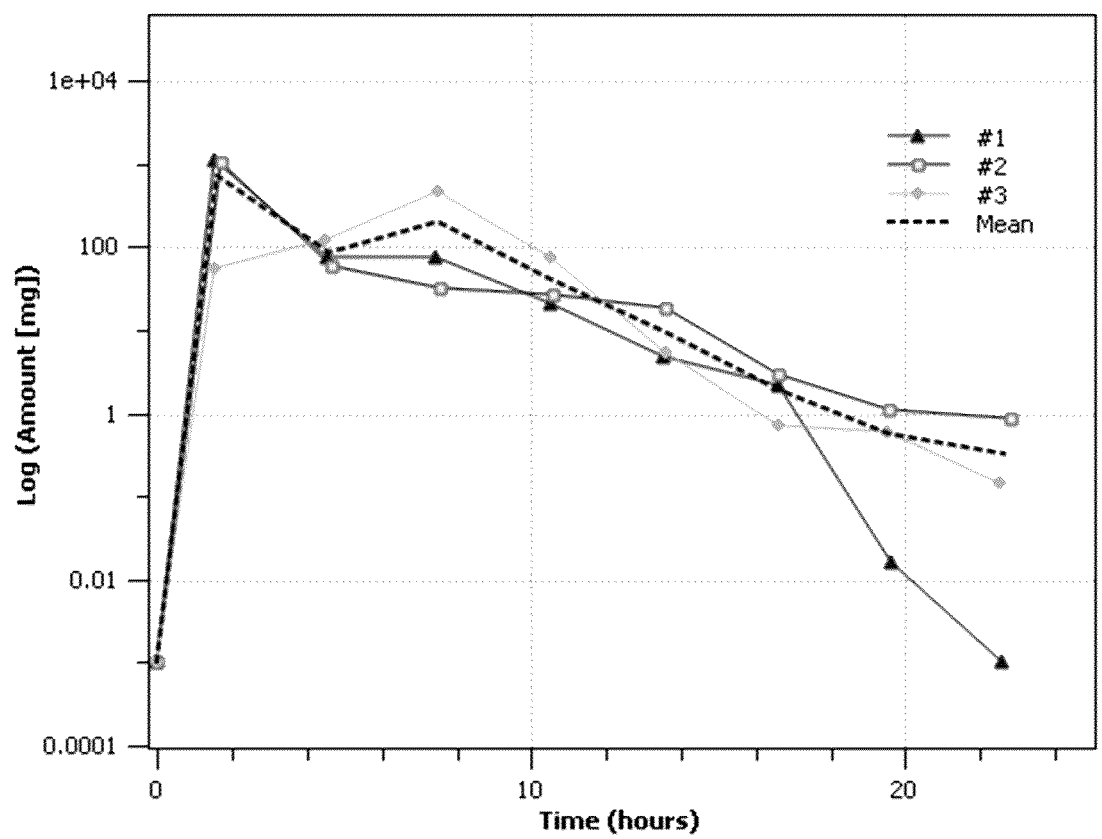
FIG. 3 shows a semi log plot of amount of gemcitabine (mg) excreted per collection interval (mean plotted) after administration of a gemcitabine paste into the renal pelvis (1000 mg/pig).

To calculate PK parameters for urine, a non-compartmental analysis was run using Phoenix 64™ (Build 6.3.0.395) WinNonlin 6.3™. Concentration vs. time data is presented in FIG. 3. The pharmacokinetic parameters area under the rate of excretion versus midpoint of time interval curve (AURC), terminal half-life ($t_{1/2}$), terminal rate constant ($k_{el}$ or $\lambda_z$), maximum rate of excretion (Rate max) and drug % recovered (Recovered) and total urine volume collected are shown in TABLE 4.

TABLE 4

Non-compartmental PK parameters for urine data, after injection of a gemcitabine paste into the renal pelvis.

| Parameter | Unit | Value |
|---|---|---|
| $AURC_{0-inf}$ | mL · µg/mL | 873583.2 ± 132794.4 |
| $t_{1/2\ (terminal)}$ | h | 2.1 ± 0.6 |
| $k_{el}$ | 1/h | 0.35 ± 0.1 |
| Rate max | µg/h | 279857.1 ± 105042.8 |

TABLE 4-continued

Non-compartmental PK parameters for urine data, after injection of a gemcitabine paste into the renal pelvis.

| Parameter | Unit | Value |
|---|---|---|
| Recovered | % | 107.3 ± 29.2 |
| Total urine | mL | 1230.3 ± 145.9 |

Example 3: Tissue Data—Extraction of Gemcitabine

Figure 4:
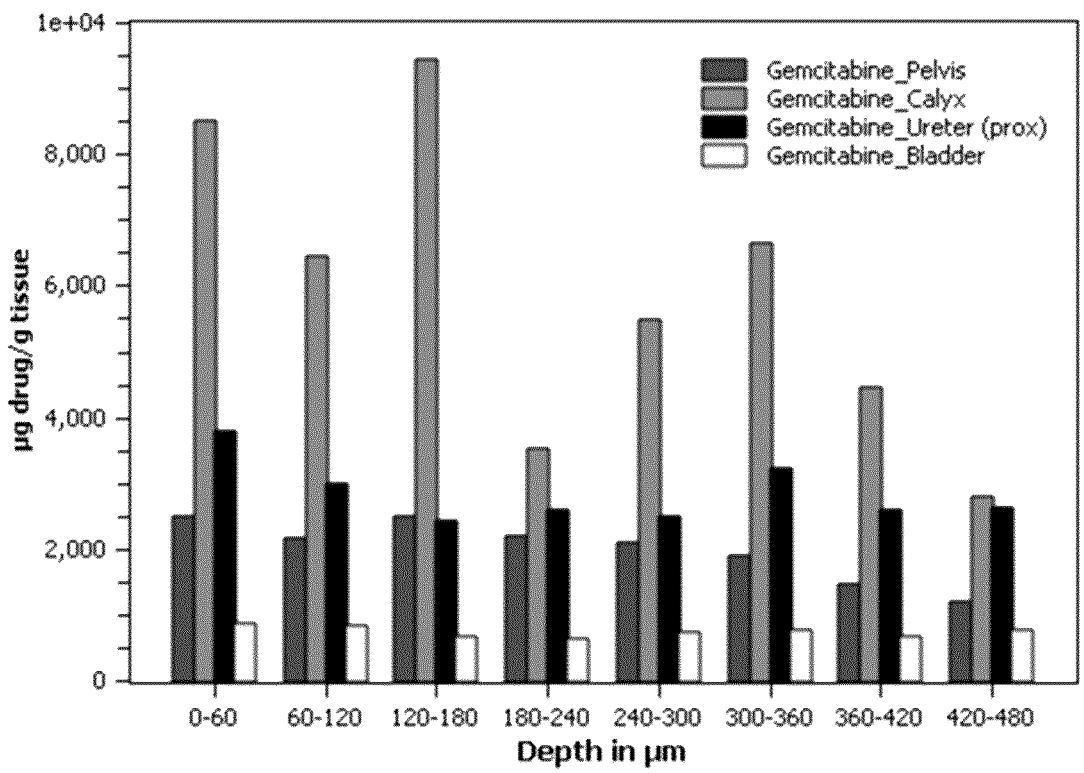
FIG. 4 shows gemcitabine tissue concentrations after the administration of gemcitabine paste into the renal pelvis. Renal tissue was collected after 1 h in vivo drug exposure (one sample per tissue).
Figure 5:
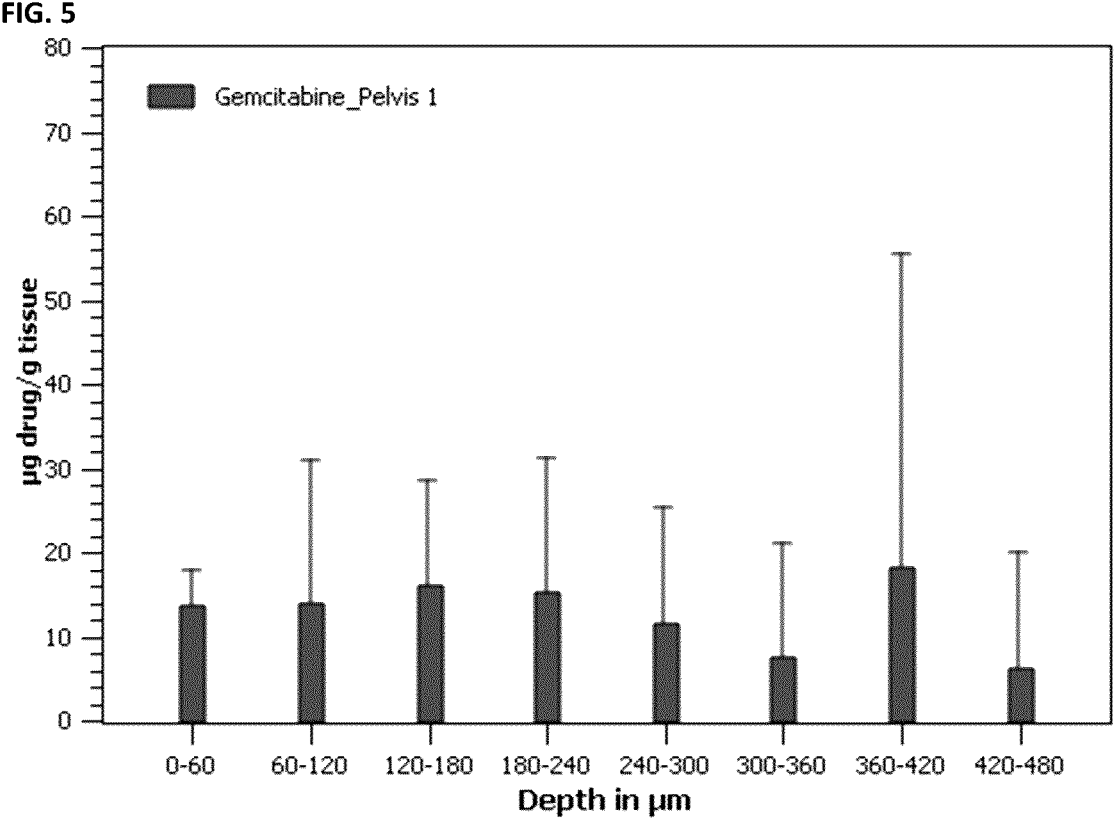
FIG. 5 shows gemcitabine tissue concentrations after the administration of gemcitabine paste into the renal pelvis. Renal tissue was collected after 3 h in vivo drug exposure (n=4).

After nephrectomy, the kidneys were cut open and tissue was collected from the upper, mid and lower section of the pelvis and calyces, from the proximal, mid and distal ureter and from the bladder. For sectioning, the tissue samples were mounted on a drop of Cryomatrix™ and cut in slices of 30 μm thickness. Two slices were collected in each of the 8 tubes to create a depth profile of 0-60, 60-120, 120-180, 180-240, 240-300, 300-360, 360-420, 420-480 μm. For tissue extraction, 500 μL of 50/50 methanol/water was added, tubes were vortexed tip sonicated and spun, then the supernatant directly measured using HPLC/UV. The tissue concentrations for the 1 h-exposed tissues were quite high at 2000-8000 μg/g tissue (FIG. 4). For the 3 h-exposed tissues, gemcitabine tissue concentrations were around 5-10 μg/g tissue (FIG. 5).

Example 4: Renal Pelvis Injection Vs. Intravenous Gemcitabine

Figure 6:
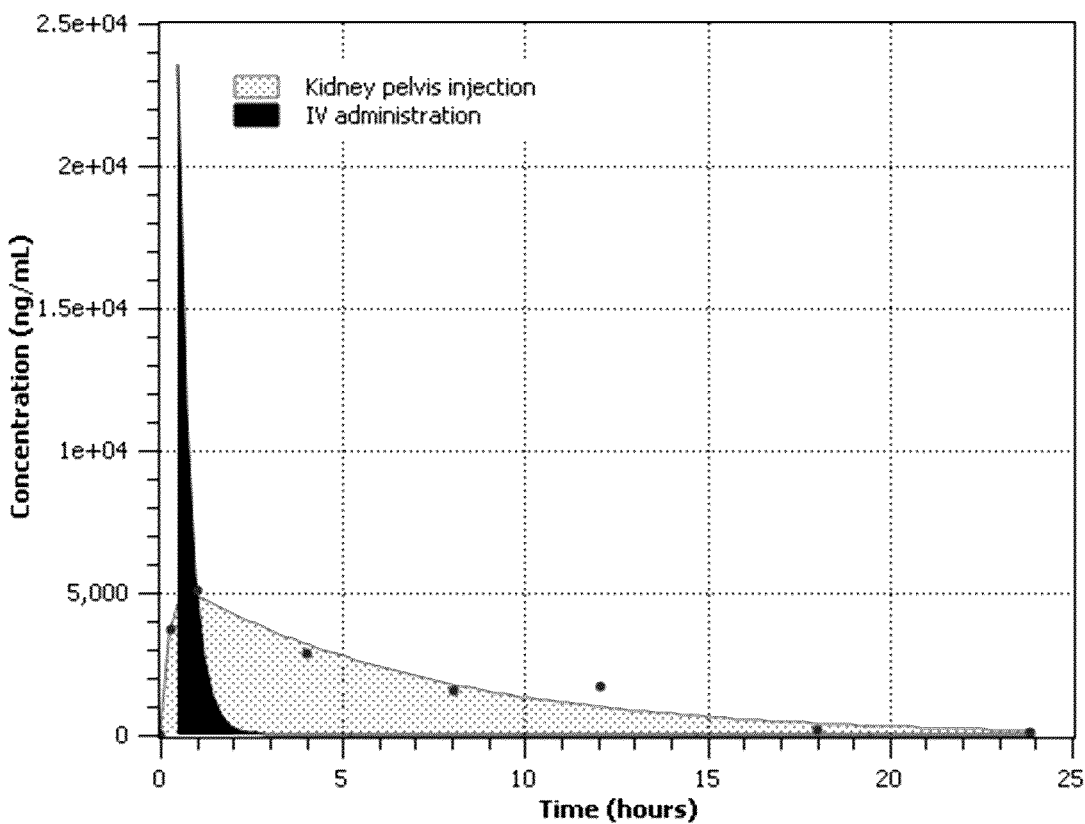
FIG. 6 shows serum data after administration of gemcitabine HCl (~30 mg/kg) after IV administration and after local administration into the renal pelvis: Renal pelvis injection: pig serum data (exponential fit of measured serum levels, n=3), intravenous administration: approximation of an IV profile using literature pharmacokinetic (PK) parameters derived from 30 min gemcitabine HCl infusions in 12 patients and a 1-compartmental model.

When comparing the serum data after injection of gemcitabine into the kidney pelvis with serum data after intravenous administration of gemcitabine, there are pronounced differences between $c_{max}$, AUC and the terminal half-life $t_{1/2}$. To visualize the differences, data from Liston et al. (Liston and Davis 2017) was used to model a representative dataset for intravenous administration and compare it to the extravascular dataset. Literature values from (Liston and Davis 2017; Dy et al. 2005) are listed in TABLE 5. The dose, $c(0.5\ h)=c_{max}$, V and $k_{el}$ were used to plot the data using a 1-compartmental approximation (FIG. 6) after the end of infusion (0.5 h).

TABLE 5

Literature PK parameters for 30 min infusion of gemcitabine (IV) and the PK parameters of the current experiment after gemcitabine paste injection into the renal pelvis.

| Parameter | Unit | Value | | |
|---|---|---|---|---|
| Dose | 1250 mg/m² | | 1000 mg/pig | |
| | (32.1 mg/kg) | | (26.4 mg/kg) | |
| $C_{max}$ | 23500 ng/mL | | 5532 ng/mL | |
| $AUC_{0-inf}$ | 12500 ng · h/mL | | 37839 ng · h/mL | |
| $t_{1/2\ (terminal)}$ | 0.23 h | | 4.12 h | |
| Clearance | 25.9 L ($V_{ss}$) | | 4.5 L/kg ($V_d$) | |
| $k_{el}$ | 3.18 1/h | | 0.18 1/h | |

Overall, the profile of the kidney injection speaks for a sustained absorption of gemcitabine from the renal pelvis into the blood stream. It can be hypothesized that the injected paste delivers gemcitabine into the tissue for multiple hours, since the half-life is extended to around 4 h from 0.2 h when compared to an intravenous injection (Liston and Davis 2017; Fogli et al. 2002). From a safety evaluation, the spike observed for intravenous administration at 23,000 ng/mL is absent but the overall exposure to gemcitabine is larger (AUC).

The formulation and procedure was tolerated well and only caused mild, transient hydronephrosis without clinical relevant increase in serum creatinine. Urine gemcitabine concentrations were highest in the first collection interval and 100% of gemcitabine was recovered in the urine within 24 hours. Serum peak concentrations ($c_{max}$) of gemcitabine were low at 5500 ng/mL but extended, with a terminal half-life ($t_{1/2}$) of 4.1 hours, mean residence time (MRT) of 6.7 hours and an overall area under the curve (AUC) of 37,800 h·ng/mL. One hour post instillation, the formulation was still detectable within the upper urinary tract and gemcitabine tissue concentrations of calyxes, pelvis and ureter at one and three hours were supportive of this extended drug exposure.

The preclinical evaluation of a mucoadhesive formulation of gemcitabine for instillation into the upper urinary tract showed promising results regarding tolerability and safety. The administration of this formulation into the kidney pelvis lead to locally high and extended gemcitabine concentrations with overall low systemic uptake. Such a pharmacokinetic profile could be advantageous for the treatment of upper urothelial tract malignancies and support further clinical evaluation.

Example 5: Manufacture of Pastes with Various Hydrophobic and Mucoadhesive Polymers Polymeric pastes were prepared according to TABLES 6-10. Compositions were warmed to 60° C. without the mucoadhesive agent and stirred. Once a homogenous formulation was achieved, the mucoadhesive polymer was suspended in the formulation. The compositions were then observed for homogeneity, viscosity, gelling characteristics, mucoadhesion and injectability using the lead formulation A as a comparison.

The polymers PLGA, PLA and PCL were dispersed homogenously or dissolved in the PEG based paste with various degrees of opacity. The addition of CMC, HA, or alginic acid had little effect on viscosity and all pastes appeared cloudy due to the presence of suspended solids. Increasing the amount of PLGA resulted in a slight decrease in viscosity. Overall, all pastes had very similar viscosities to formulation A except the addition of carbomer, which caused a significant increase in viscosity. These compositions and results are summarized in TABLE 11.

TABLE 6

Compositions of formulations with different mucoadhesive agents

| | % (weight) Formulation | | | | | |
|---|---|---|---|---|---|---|
| Excipient | A | B1 | B2 | B3 | B4 | B5 |
| PEG 300 | 78 | 78 | 78 | 78 | 78 | 79 |
| PEG 1000 | 14 | 14 | 14 | 14 | 14 | 15 |
| PLGA[1] | 5 | 5 | 5 | 5 | 5 | 6 |
| Hyaluronic Acid (high MW[2]) | 3 | — | — | — | — | — |
| Sodium Carboxymethylcellulose | — | 3 | — | — | — | — |
| Carbomer 940 | — | — | 3 | — | — | — |
| Alginic Acid | — | — | — | 3 | — | — |
| Hyaluronic Acid (low MW) | — | — | — | — | 3 | — |

[1]50:50 Poly(DL-lactic-co-glycolic)acid (IV 0.15-0.25 dL/g)
[2]MW molecular weight

TABLE 7

Compositions of formulations with increasing amounts of hyaluronic acid

| | % (weight) Formulation | | | | |
|---|---|---|---|---|---|
| Excipient | F1 | F2 | A | F3 | F4 |
| PEG 300 | 79 | 78.5 | 78 | 77.5 | 77 |
| PEG 1000 | 15 | 14.5 | 14 | 13.5 | 13 |
| PLGA[1] | 5 | 5 | 5 | 5 | 5 |
| Hyaluronic Acid (high MW[2]) | 1 | 2 | 3 | 4 | 5 |

[1] 50:50 Poly(DL-lactic-co-glycolic)acid (IV 0.15-0.25 dL/g)
[2] MW molecular weight

TABLE 8

Compositions of formulations with different drugs

| | % (weight) Formulation | | | |
|---|---|---|---|---|
| Excipient | A | A1 | A2 | A3 |
| PEG 300 | 78 | 99 | 99.7 | 99 |
| PEG 1000 | 14 | — | — | — |
| PLGA[1] | 5 | — | — | — |
| Hyaluronic Acid (high MW[2]) | 3 | — | — | — |
| Gemcitabine HCl | — | 1 | — | — |
| Docetaxel | — | — | 0.3 | — |
| Albumin | — | — | — | 1 |

[1] 50:50 Poly(DL-lactic-co-glycolic)acid (IV 0.15-0.25 dL/g)
[2] MW molecular weight

TABLE 9

Compositions of formulations with different hydrophobic polymers

| | % (weight) Formulation | | | |
|---|---|---|---|---|
| Excipient | A | C | D | D1 |
| PEG 300 | 78 | 78 | 78 | 78 |
| PEG 1000 | 14 | 14 | 14 | 14 |
| PLGA[1] | 5 | — | — | — |
| PCL[3] | — | 5 | — | — |
| PLA[4] (high MW[2]) | — | — | 5 | — |
| PLA (low MW) | — | — | — | 5 |
| Hyaluronic Acid (high MW) | 3 | 3 | 3 | 3 |

[1] 50:50 Poly(DL-lactic-co-glycolic)acid (IV 0.15-0.25 dL/g)
[2] MW molecular weight
[3] PCL Poly(ε-caprolactone)
[4] PLA Polylactic acid

TABLE 10

Compositions of formulations with increasing amounts of hydrophobic polymer

| | % (weight) Formulation | | | |
|---|---|---|---|---|
| Excipient | A | E1 | E2 | E3 |
| PEG 300 | 78 | 75.5 | 73 | 80.5 |
| PEG 1000 | 14 | 11.5 | 9 | 16.5 |
| PLGA[1] | 5 | 10 | 15 | — |
| Hyaluronic Acid (high MW[2]) | 3 | 3 | 3 | 3 |

[1] 50:50 Poly(DL-lactic-co-glycolic)acid (IV 0.15-0.25 dL/g)
[2] MW molecular weight

TABLE 11

Observations on compositions regarding homogeneity, viscosity, gelling, mucoadhesion and injectability compared to composition A.

| Composition | Homogeneity Score[1] | Viscosity Score[2] | Gelling Score[3] | Mucoadhesion Score[4] | Injectability Score[5] |
|---|---|---|---|---|---|
| B1 (CMC) | 1 | 1 | 1 | 1 | 1 |
| B2 (Carbomer) | − | + | 1 | 1 | − |
| B3 (Alginic Acid) | 1 | 1 | − | − | 1 |
| B4 (Hyaluronic Acid, low MW) | 1 | 1 | 1 | 1 | 1 |
| B5 (none) | 1 | 1 | − | − | 1 |
| C (PCL) | − | n/a | n/a | n/a | − |
| D (PLA, high MW) | − | n/a | n/a | n/a | − |
| D1 (PLA, low MW) | − | n/a | n/a | n/a | − |
| E1 (medium high PLGA) | 1 | − | n/a | n/a | 1 |
| E2 (high PLGA) | 1 | − | n/a | n/a | 1 |
| E3 (no PLGA) | 1 | 1 | n/a | n/a | 1 |
| F1 (1% HA) | 1 | 1 | − | 1 | 1 |
| F2 (2% HA) | 1 | 1 | − | 1 | 1 |
| F3 (4% HA) | 1 | 1 | 1 | 1 | 1 |
| F4 (5% HA) | 1 | 1 | + | 1 | 1 |

[1] 1 = similar homogeneity, − = less homogenous
[2] 1 = similar viscosity, + = more viscous, − = less viscous
[3] 1 = similar gelling characteristics, + = gels more, − = gels less
[4] 1 = similar adhesion, + = adheres more, − = adheres less
[5] 1 = similar injectability, + = easier injectability, − = more difficult injectability

Example 6: Mucoadhesion, the Mucoadhesive Effect of Pastes Containing Different Mucoadhesive Polymers The pastes were made up containing 3% by weight of the mucoadhesive polymers HA, CMC, Carbomer, Alginic acid or no mucoadhesive polymer with 5% PLGA and 92% PEG. Furthermore pastes with increasing amounts of HA were prepared (1, 2, 3, 4, 5%). Pieces of renal pelvis were cut from frozen pig kidneys and kept moist with PBS (pH 7.4). 250 mg of formulation was placed on top of each tissue sample. The samples were covered and kept at 37° C. for 5 minutes. Tissue samples were then rinsed with excess water and dyed in a dilute methylene blue solution for 1 min, then rinsed again. At this time any remaining paste was scrapped off the tissue to reveal the level of unstained tissue. Using this method, any tissue that was not covered in a coating of mucoadhesive paste was stained blue. All pastes showed a clear demarcation of color on the tissue whereby peripheral edges not coated with paste were stained blue and the paste-covered area was pink-tissue colored. Control tissues (both no paste or paste with no mucoadhesive polymer) were fully stained blue (images not shown), however, these results are summarized in TABLE 11 using the mucoadhesion score compared to formulation A.

Figure 12:
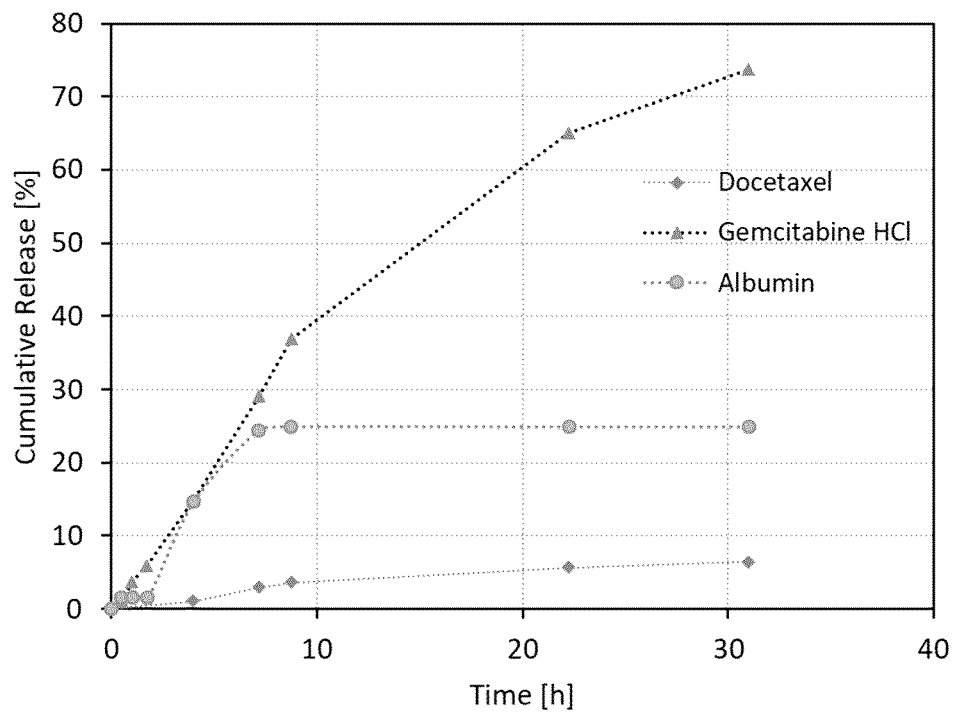
FIG. 12 shows the release of docetaxel, gemcitabine HCl and albumin from formulation A (TABLE 8).

Example 7: Drug Release Studies: The Use of the Lead Formulation for the Controlled Release of Hydrophilic, Hydrophobic and Biological Drugs Formulation A of PLGA 5%, HA 3%, PEG 92% was made up as described in TABLE 8. Gemcitabine HCl, docetaxel or bovine serum albumin (BSA—used as a protein model for a biological therapeutic agent) was levigated into the paste at a loading (% w/w) of 1, 0.3 and 1 (respectively) using a spatula until a fully homogenous mixture was formed. 100 mg of each formulation was placed in a dialysis cut off mini chamber (Millipore™) with a cut off of 7000 Da. For the protein study the mini chamber was not closed but a small retaining sponge applied. The chamber was placed in 5 mL of PBS (pH 7.4 or PBS containing albumin to increase the solubility of docetaxel) and placed in an incubator at 37° C. At defined time points all the PBS was removed and the amount of gemcitabine and docetaxel in the release media quantitated using HPLC methods (isocratic elution at 1 mL/min, wavelengths: 254 nm and 228 nm, retention time: 2.1 min and 7.1 min) or a Bradford assay for the protein. All drugs released form the pastes in a controlled manner over 30 hours as shown in FIG. 12. The release of gemcitabine was faster than the other two agents but all drugs were still releasing at 30 hours.

Viscosity

Pastes were manufactured as described in TABLES 6-10. Using an Anton Parr MCR72™ viscometer, the software: RheoCompass 1.20™, a parallel plate 25 mm geometry (Measuring system PP25) and a gap size of 0.5 mm, flow curves (rotational shear rates between 1-100 1/s) were determined at ambient temperature (20-25° C.) and analyzed using a power-law fit. In separate experiments, the pastes were hydrated with an equal weight of water and left to equilibrate for 5-10 minutes. Using the same measurement system as above, viscosities of the gels were determined using oscillations at 1 Hz and a strain between 0.01 and 100%.

The determinations were made using a shear rate of 1 to 100 1/s and strain of 0.01 to 100%. For most samples the viscosity was higher at very low stress rates but dropped at higher shear rates or higher stress. This type of shear thinning may reflect an easier injection using higher pressures/shear in a syringe. The viscosity graphs are shown in FIGS. 7-11 and a viscosity score is given to the samples and summarized in in TABLE 11.

Viscosities of Non Hydrated Samples

Figure 7:
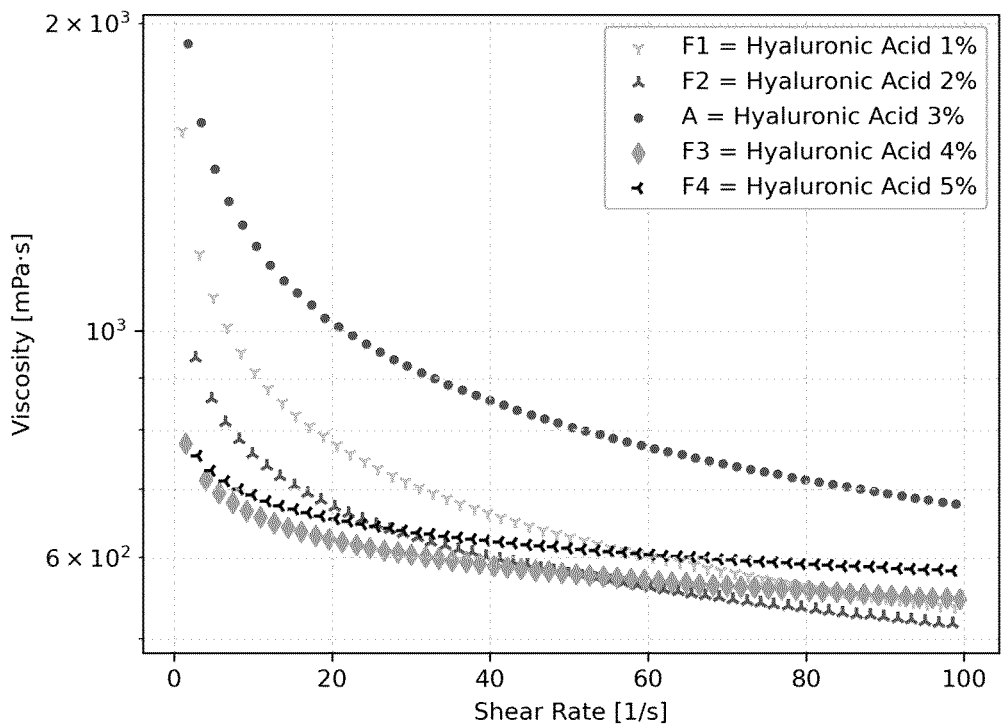
FIG. 7 shows the viscosities of formulations A, F1, F2, F3, F4 (TABLE 7) at ambient temperature BEFORE mixing them with water.
Figure 10:
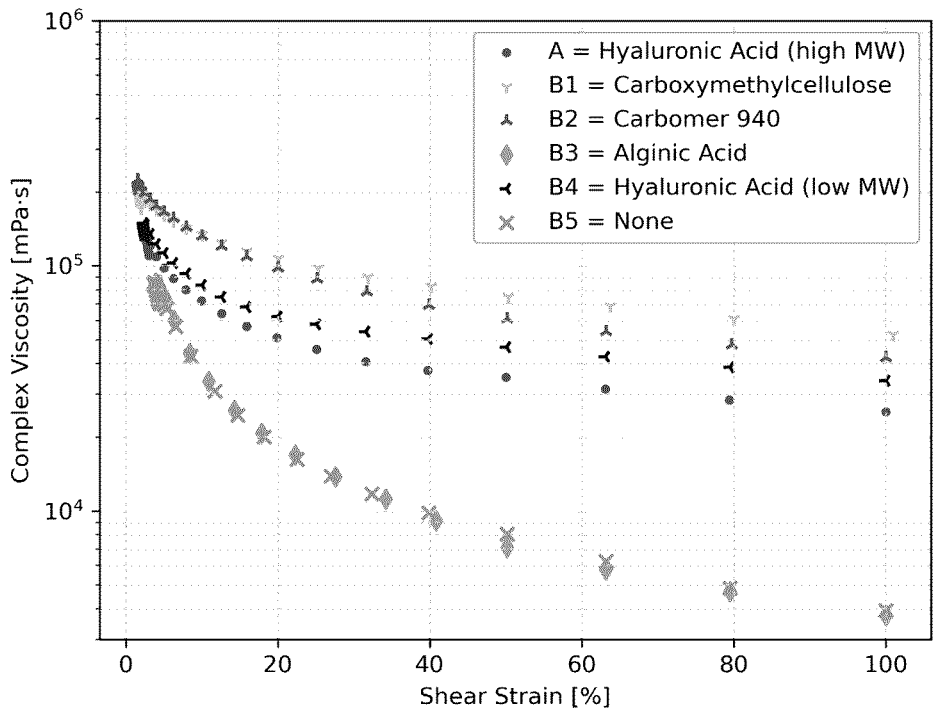
FIG. 10 shows the viscosities of formulations A, B1, B2, B2, B4, B5 (TABLE 6) at ambient temperature AFTER mixing them 1:1 with water.
Figure 11:
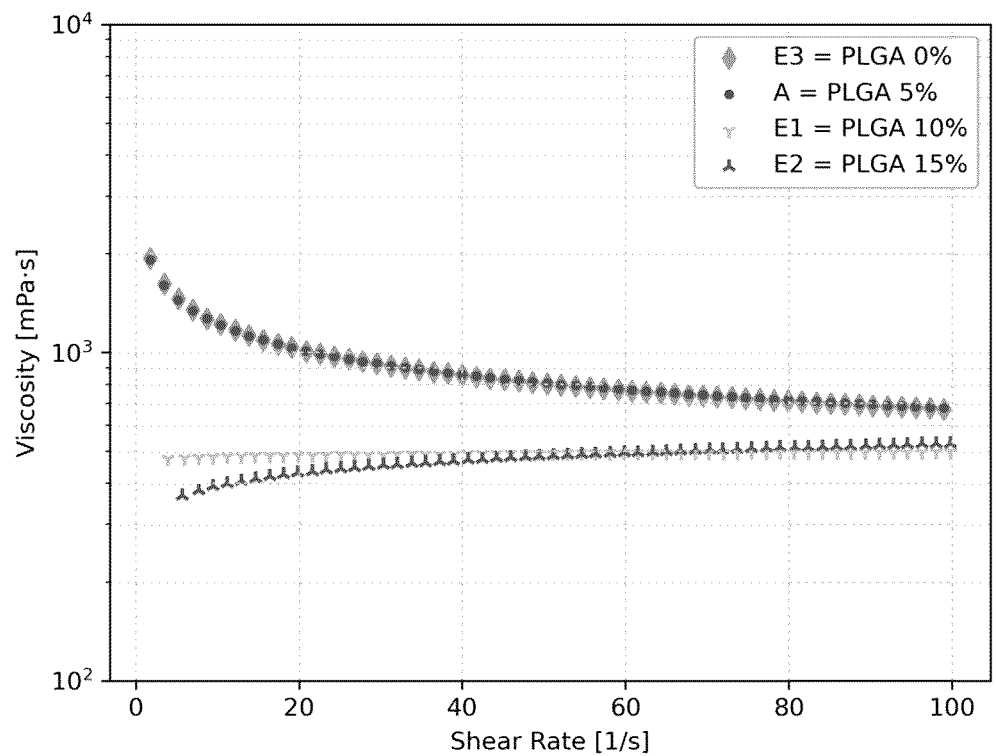
FIG. 11 shows the viscosities of formulations A, E1, E2, E3 (TABLE 10) at ambient temperature.

The addition of PLGA at 5% had no effects on viscosity at low or high shear rates. However at 10 and 15% PLGA loadings pastes were less viscous (FIG. 11). These data demonstrate that all PLGA containing pastes would function well as injectable pastes. The addition of CMC, Carbomer, Alginic acid or HA (each at 3% loading and HA separately also at 1, 2, 3, 4, 5%) allowed for slightly higher viscosities of pastes as compare to pastes with no mucoadhesive component but all values were very similar (FIGS. 7 and 10). These data demonstrate that the addition of mucoadhesive components to the paste did not impact injectability. Although the addition of carbomer caused a net increase in viscosity, the paste remained fluid enough to manipulate with a spatula indicating that it could be loaded into a syringe for injection or extrusion. Using HA, the addition of increasing concentrations of this polysaccharide resulted in little difference in viscosity of the paste demonstrating that HA would have no effect on injectability.

Viscosities of Hydrated Samples

Figure 8:
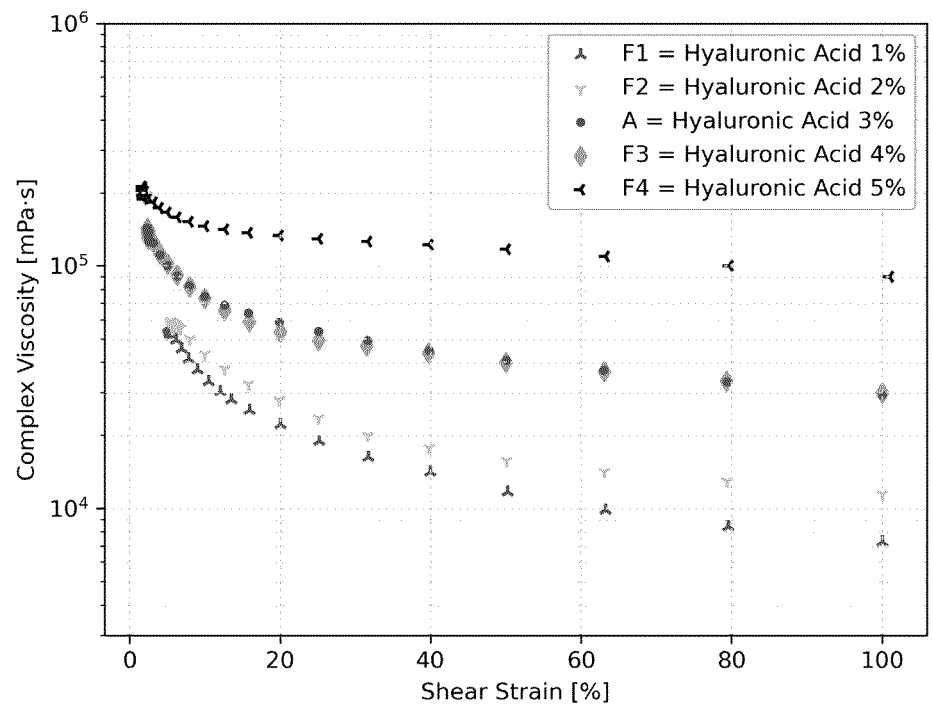
FIG. 8 shows the viscosities of formulations A, F1, F2, F3, F4 (TABLE 7) at ambient temperature AFTER mixing them 1:1 with water.
Figure 9:
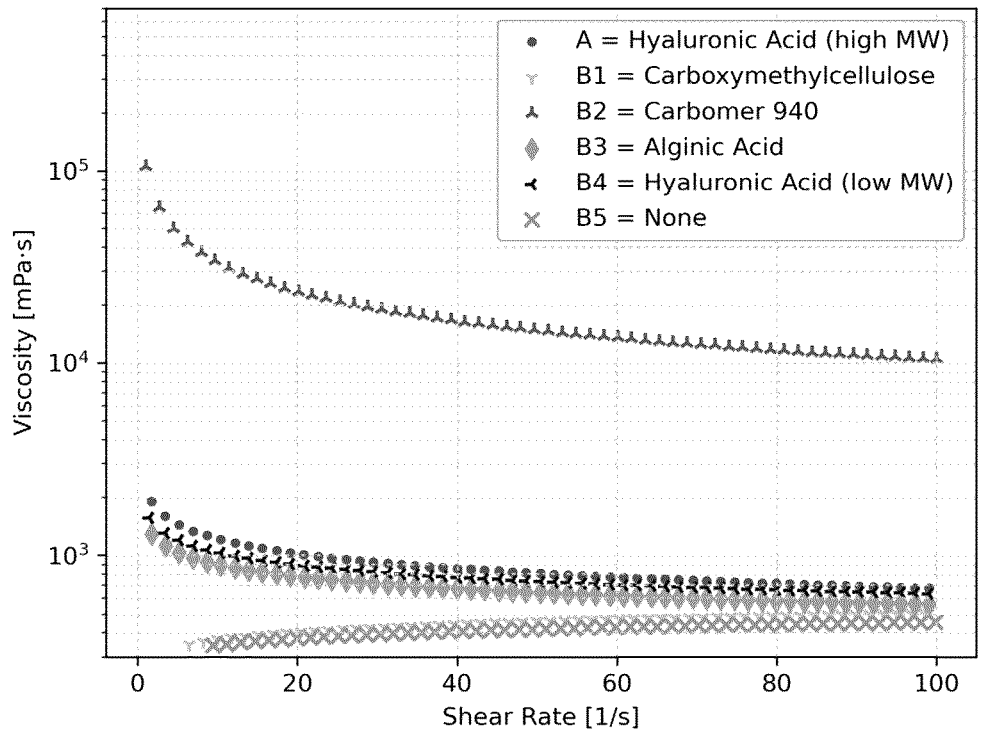
FIG. 9 shows the viscosities of formulations A, B1, B2, B2, B4, B5 (TABLE 6) at ambient temperature BEFORE mixing them with water.

All hydrated pastes had increased viscosity as compared to non-hydrated. These data do not reflect injectability since the paste would only become hydrated after injection. These values (approx. 80,000 to 100,000 mPa·s) were similar for all pastes at low strain and at high strain, pastes containing HAs, CMC, and Carbomer had higher viscosities than control or alginic acid pastes (FIGS. 8 and 10). The addition of increasing amounts of HA caused a concentration dependent increase in the viscosity for all pastes at both high and low shear strain.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

Athanasiou, K A, G G Niederauer, and C M Agrawal. 1996. "Sterilization, Toxicity, Biocompatibility and Clinical Applications of Polylactic Acid/Polyglycolic Acid Copolymers." *Biomaterials* 17 (2): 93-102. http://www.sciencedirect.com/science/article/pii/0142961296857541.

Audenet, F, D R Yates, O Cussenot, and M Roupret. 2013. "The Role of Chemotherapy in the Treatment of Urothelial Cell Carcinoma of the Upper Urinary Tract (UUT- UCC)." *Urol Oncol* 31 (4): 407-13. https://doi.org/10.1016/j.urolonc.2010.07.016.

Bouissou, C, J J Rouse, R Price, and van der C F Walle. 2006. "The Influence of Surfactant on PLGA Microsphere Glass Transition and Water Sorption: Remodeling the Surface Morphology to Attenuate the Burst Release." *Pharmaceutical Research* 23 (6): 1295-1305. https://doi.org/10.1007/s11095-006-0180-2.

Dunn, Richard L. 2002. "The Atrigel Drug Delivery System." In *Modified-Release Drug Delivery Technology*, 647-55. Informa Healthcare. https://doi.org/doi:10.1201/9780203910337.ch5410.1201/9780203910337.ch54.

Dy, Grace K., Ajit Suri, Joel M. Reid, Jeff A. Sloan, Henry C. Pitot, Steven R. Alberts, Richard M. Goldberg, et al. 2005. "A Phase IB Study of the Pharmacokinetics of Gemcitabine and Pemetrexed, When Administered in Rapid Sequence to Patients with Advanced Solid Tumors." *Cancer Chemotherapy and Pharmacology* 55 (6): 522-30. https://doi.org/10.1007/s00280-004-0950-7.

Fogli, S, R Danesi, A Gennari, S Donati, P F Conte, and M Del Tacca. 2002. "Gemcitabine, Epirubicin and Paclitaxel: Pharmacokinetic and Pharmacodynamic Interactions in Advanced Breast Cancer." *Annals of Oncology* 13 (6): 919-27. https://doi.org/10.1093/annonc/mdf164.

Gitlitz, B J, C Baker, Y Chapman, H J Allen, L D Bosserman, R Patel, J D Sanchez, R M Shapiro, and R A Figlin. 2003. "A Phase II Study of Gemcitabine and Docetaxel Therapy in Patients with Advanced Urothelial Carcinoma." *Cancer* 98 (9): 1863-69. https://doi.org/10.1002/cncr.11726.

Gontero, Paolo, and Alessandro Tizzani. 2007. "Intravesical Gemcitabine: State of the Art." *European Urology, Supplements*. Elsevier. https://doi.org/10.1016/j.eursup.2007.05.002.

Jackson, John K, Martin E Gleave, Virginia Yago, Eliana Beraldi, William L Hunter, and Helen M Burt. 2000. "The Suppression of Human Prostate Tumor Growth in Mice by the Intratumoral Injection of a Slow-Release Polymeric Paste Formulation of Paclitaxel." *Cancer Research* 60 (15): 4146. http://cancerres.aacrjournals.org/content/60/15/4146.abstract.

Jackson, John K, Tawny Hung, Kevin Letchford, and Helen M Burt. 2007. "The Characterization of Paclitaxel-Loaded Microspheres Manufactured from Blends of Poly (Lactic-Co-Glycolic Acid)(PLGA) and Low Molecular Weight Diblock Copolymers." *International Journal of Pharmaceutics* 342 (1): 6-17.

Jackson, John K, Janet Smith, Kevin Letchford, Kelly Anne Babiuk, Lindsay Machan, Pierre Signore, William L Hunter, Kaiyue Wang, and Helen M Burt. 2004. "Characterization of Perivascular Poly(Lactic-Co-Glycolic Acid) Films Containing Paclitaxel." *International Journal of Pharmaceutics* 283 (1-2): 97-109. https://doi.org/http://dx.doi.org/10.1016/j.ijpharm.2004.06.025.

Jain, Rajeev A. 2000. "The Manufacturing Techniques of Various Drug Loaded Biodegradable Poly(Lactide-Co-Glycolide) (PLGA) Devices." *Biomaterials, Orthopaedic Polymeric Biomaterials: Basic Aspects of Biodegradables*, 21 (23): 2475-90. https://doi.org/10.1016/S0142-9612(00)00115-0.

Konorty, M., and G. Hakim. 2014 Material and method for treating internal cavities. U.S. Pat. No. 10,471,150.

Liston, Dane R., and Myrtle Davis. 2017. "Clinically Relevant Concentrations of Anticancer Drugs: A Guide for Nonclinical Studies." *Clinical Cancer Research*. American Association for Cancer Research Inc. https://doi.org/10.1158/1078-0432.CCR-16-3083.

Lughezzani, G, M Burger, V Margulis, S F Matin, G Novara, M Roupret, S F Shariat, C G Wood, and R Zigeuner. 2012. "Prognostic Factors in Upper Urinary Tract Urothelial Carcinomas: A Comprehensive Review of the Current Literature." *European Urology* 62 (1): 100-114. https://doi.org/10.1016/j.eururo.2012.02.030.

Maffezzini, Massimo, Fabio Campodonico, Matteo Puntoni, Antonietta Martelli, and Francesca Mattioli. 2009. "Systemic Absorption and Pharmacokinetics of Single-Dose Intravesical Gemcitabine After Transurethral Resection of the Bladder in Non-Muscle-Invasive Bladder Cancer." *Urology* 74 (5): 1078-83. https://doi.org/10.1016/j.urology.2009.05.094.

Makadia, Hirenkumar K, and Steven J Siegel. 2011. "Poly Lactic-Co-Glycolic Acid (PLGA) as Biodegradable Controlled Drug Delivery Carrier." *Polymers* 3 (3): 1377-97. https://doi.org/10.3390/polym3031377.

Pauletti, G. M. 2004 Therapeutic Compositions for Drug Delivery to and Through Covering Epithelia. US 2004/0151774.

Roupret, M, M Babjuk, E Comperat, R Zigeuner, R Sylvester, M Burger, N Cowan, et al. 2013. "European Guidelines on Upper Tract Urothelial Carcinomas: 2013 Update." *European Urology* 63 (6): 1059-71. https://doi.org/10.1016/j.eururo.2013.03.032.

Roy, S., K. Pal, A. Anis, K. Pramanik, and B. Prabhakar. 2009. "Polymers in Mucoadhesive Drug-Delivery Systems: A Brief Note." *Designed Monomers and Polymers*. Taylor & Francis Group. https://doi.org/10.1163/138577209X12478283327236.

Siegel, Steven J, Jonathan B Kahn, Kayla Metzger, Karen I Winey, Kathryn Werner, and Nily Dan. 2006. "Effect of Drug Type on the Degradation Rate of PLGA Matrices." *European Journal of Pharmaceutics and Biopharmaceutics* 64 (3): 287-93. https://doi.org/10.1016/j.ejpb.2006.06.009.

Winternitz, Charles I, John K Jackson, Ann Marie Oktaba, and Helen M Burt. 1996. "Development of a Polymeric Surgical Paste Formulation for Taxol." *Pharmaceutical Research* 13 (3): 368-75. https://doi.org/10.1023/A:1016032207246.

Witjes, J. A., A. G. Van Der Heijden, J. L. J. Vriesema, G. J. Peters, A. Laan, and J. A. Schalken. 2004. "Intravesical Gemcitabine: A Phase 1 and Pharmacokinetic Study." *European Urology* 45 (2): 182-86. https://doi.org/10.1016/j.eururo.2003.09.014.

Yu, L., and J. G. Ferguson. Liquid formulation compositions, medicament delivery devices, and methods of preparation and use thereof. WO2016019627.

What is claimed is:

1. A composition, the composition comprising:
   (a) a polyethylene glycol (PEG) composition that is between about 85% and about 96% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight higher than the first low molecular weight PEG and between about 500 Da and about 2,000 Da;
   (b) a water insoluble polymer that is between about 2% and about 10% by weight, wherein the water insoluble polymer is selected from one or more of: poly lactic-co-glycolic acid (PLGA), poly (E-caprolactone) (PCL), and polylactic acid (PLA); and (c) a mucoadhesive polymer that is between about 2% and about 5% by weight.

2. The composition of claim 1, wherein the water insoluble polymer is PLGA.

3. The composition of claim 1, wherein the water insoluble polymer is PLGA, and wherein the molar ratio of the monomers of lactic acid to glycolic acid is between 90:10 and 50:50.

4. The composition of claim 1, wherein the mucoadhesive polymer is selected from one or more of the following: hyaluronic acid; poly (acrylic acid) and poly (methacrylic acid) derivatives; cyanoacrylates; poly (acrylic acid); sodium carboxymethylcellulose; hydroxypropylcellulose; polycarbophil; chitosan; alginate; gellan; xanthan; thiolated poly (acrylic acid); poloxamer; celluloseacetophthalate; ethylcellulose; methyl cellulose; hydroxy ethyl cellulose; poly (amidoamine) dendrimers; poly (dimethyl siloxane); and poly (vinyl pyrrolidone).

5. The composition of claim 1, wherein mucoadhesive polymer is hyaluronic acid.

6. The composition of claim 1, wherein the first low molecular weight PEG is selected from one of the following: PEG 200; PEG 300; PEG 400; and PEG 500.

7. The composition of claim 1, wherein the second low molecular weight PEG is selected from one of the following: PEG 500; PEG 600; PEG 700; PEG 800; PEG 900; PEG 1000; PEG 1100; PEG 1200; PEG 1300; PEG 1400; PEG 1500; PEG 1600; PEG 1700; PEG 1800; PEG 1900; and PEG 2000.

8. The composition of claim 1, wherein the PEG composition, further comprises one or more low molecular weight PEG selected from one or more of the following: PEG 200; PEG 300; PEG 400; PEG 500; PEG 600; PEG 700; PEG 800; PEG 900; PEG 1000; PEG 1100; PEG 1200; PEG 1300; PEG 1400; PEG 1500; PEG 1600; PEG 1700; PEG 1800; PEG 1900; and PEG 2000.

9. The composition of claim 1, wherein the PEG has an average molecular weight between about 200 Da and about 2,000 Da.

10. The composition of claim 1, further comprising one or more drug compounds or pharmaceutically acceptable salt, solvate or solvate of the salt thereof.

11. The composition of claim 10, wherein the one or more drug compounds or pharmaceutically acceptable salt, solvate or solvate of the salt thereof is selected from one or more of the following categories: anti-cancer drugs; anti-inflammatory agents; anti-bacterial drugs; anti-viral drugs; anti-proliferative drugs; anti-fibrotic drugs; anesthetic drug; neuromodulatory drugs; and
analgesics.

12. The composition of claim 10, wherein the one or more drug compounds or pharmaceutically acceptable salt, solvate or solvate of the salt thereof is an anti-cancer drug selected from one or more of the following: Actinomycin; All-trans retinoic acid; Azacitidine; Azathioprine; Bleomycin; Bortezomib; Carboplatin; Capecitabine; Cisplatin; Chlorambucil; Cyclophosphamide; Cytarabine; Daunorubicin; Docetaxel; Doxifluridine; Doxorubicin; Epirubicin; Epothilone; Etoposide; Fluorouracil; Gemcitabine; Hydroxyurea; Idarubicin; Imatinib; Irinotecan; Mechlorethamine; Mercaptopurine; Methotrexate; Mitoxantrone; Oxaliplatin; Paclitaxel; Pemetrexed; Teniposide; Tioguanine; Topotecan; Valrubicin; Vemurafenib; Vinblastine; Vincristine; Vindesine; and Vinorelbine,
wherein the drug is gemcitabine HCl,
wherein the one or more drug compounds or pharmaceutically acceptable salt, solvate or solvate of the salt thereof is an anesthetic drug is a local anesthetic selected from one or more of the following: Procaine; Benzocaine; Chloroprocaine; Cocaine; Cyclomethycaine; Dimethocaine; Piperocaine; Propoxycaine; Novocaine; Proparacaine; Tetracaine; Articaine; Bupivacaine; Cinchocaine; Etidocaine; Levobupivacaine; Lidocaine; Mepivacaine; Prilocaine; Ropivacaine; and Trimecaine, and
wherein the one or more drug compounds or pharmaceutically acceptable salt, solvate or solvate of the salt thereof is an anti-bacterial drug selected from one or more of the following: penicillins, cephalosporins, polymyxins, rifamycins, lipiarmycins, quinolones, sulfonamides, macrolides, lincosamides, tetracyclines, aminoglycosides, lipopeptides, glycylcyclines, oxazolidinones, and lipiarmycins, cephalexin, cefazolin, gentamicin, ciprofloxacin, clindamycin, macrodantin, tobramycin, rifampicin, daptomycin, linezolid, vancomycin, fusidic acid, and silver compounds.

13. The composition of claim 1, wherein the mucoadhesive polymer has a molecular weight ≥50 kDa.

14. A pharmaceutical composition comprising the composition of claim 10, together with a pharmaceutically acceptable diluent or carrier.

15. A method of administering a drug to a mucosal surface area, the method comprising: (a) combining the composition of claim 1 with a drug to form a drug loaded composition, and (b) delivering the drug loaded composition to the mucosal surface area.

16. The method of claim 15, wherein the mucosal surface area is selected from one or more of the following: urogenital tract; gastrointestinal tract; and respiratory tract.

17. The method of claim 15, wherein the mucosal surface area is selected from one or more of the following: kidney; ureter; bladder; urethra; uterus; vagina; penis; mouth; esophagus;
stomach; small intestine; large intestine; rectum; anus; nasal sinuses; pharynx; larynx; trachea;
bronchi; bronchioles; lungs.

18. The method of claim 15, wherein the drug loaded composition is for the treatment of one or more of: cancer; pain; wound; and inflammation.

19. A composition, the composition comprising:
(a) a polyethylene glycol (PEG) composition that is between about 85% and about 96% by weight, comprising (i) a first low molecular weight polyethylene glycol (PEG), wherein the first low molecular weight PEG has an average molecular weight between about 200 Da and about 500 Da, and (ii) a second low molecular weight polyethylene glycol (PEG) wherein the second low molecular weight PEG has an average molecular weight between about 500 Da and about 2,000 Da; and
(b) a mucoadhesive polymer that is between about 4% and about 15% by weight.

20. The composition of claim 19, wherein the composition further comprises a water insoluble polymer.

* * * * *